(12) United States Patent
Liu et al.

(10) Patent No.: US 8,056,419 B2
(45) Date of Patent: *Nov. 15, 2011

(54) ARTIFICIAL LATERAL LINE

(75) Inventors: Chang Liu, Winnetka, IL (US); Jonathan Engel, Minneapolis, MN (US); Jack Chen, Fremont, CA (US)

(73) Assignee: The Board of Trustees of the University of Illinois, Urbana, IL (US)

( * ) Notice: Subject to any disclaimer, the term of this patent is extended or adjusted under 35 U.S.C. 154(b) by 174 days.

This patent is subject to a terminal disclaimer.

(21) Appl. No.: 12/508,229

(22) Filed: Jul. 23, 2009

(65) Prior Publication Data

US 2010/0010754 A1    Jan. 14, 2010

Related U.S. Application Data

(63) Continuation of application No. 11/824,042, filed on Jun. 29, 2007, now Pat. No. 7,644,624, which is a continuation-in-part of application No. 10/861,096, filed on Jun. 4, 2004, now Pat. No. 7,357,035.

(60) Provisional application No. 60/817,885, filed on Jun. 30, 2006.

(51) Int. Cl.
    *G01L 7/00* (2006.01)
(52) U.S. Cl. ....................................................... 73/756
(58) Field of Classification Search .................... 73/756, 73/720, 719, 721; 422/50; 324/158.1; 702/42
    See application file for complete search history.

(56) References Cited

U.S. PATENT DOCUMENTS

| | | | |
|---|---|---|---|
| 3,645,275 | A | 2/1972 | Nolen |
| 4,611,171 | A | 9/1986 | Woods |
| 4,875,533 | A | 10/1989 | Mihara et al. |
| 4,951,510 | A | 8/1990 | Holm-Kennedy et al. |
| 5,037,515 | A | 8/1991 | Tsai et al. |
| 5,095,762 | A | 3/1992 | Holm-Kennedy et al. |
| 5,239,870 | A | 8/1993 | Kaneko |
| 5,412,994 | A | 5/1995 | Cook et al. |
| 5,483,834 | A | 1/1996 | Frick |
| 5,726,480 | A | 3/1998 | Pister |
| 5,872,320 | A | 2/1999 | Kamentser et al. |

(Continued)

FOREIGN PATENT DOCUMENTS

WO    WO-02/095785    11/2002

(Continued)

OTHER PUBLICATIONS

J. Chen, J. Zou and C. Liu, "A Surface Micromachined, Out-of-Plane Anemometer," presented at Proceedings of MEMS 02, Las Vegas, NV, 2002.

(Continued)

*Primary Examiner* — Jewel V Thompson
(74) *Attorney, Agent, or Firm* — Greer, Burns & Crain Ltd.

(57) ABSTRACT

An artificial sensor comprises at least one substrate, and a plurality of flow sensors disposed on the at least one substrate for providing a plurality of spatial-temporally varying signals representing a hydrodynamic stimulus. The plurality of flow sensors are spatially distributed on the at least one substrate. A processor is coupled to the plurality of flow sensors for receiving the signals and determining spatial-temporal information from the received signals.

16 Claims, 27 Drawing Sheets

U.S. PATENT DOCUMENTS

| | | | |
|---|---|---|---|
| 6,151,771 A | 11/2000 | Tzeng et al. | |
| 6,230,563 B1 | 5/2001 | Clark et al. | |
| 6,250,141 B1 | 6/2001 | Geyer | |
| 6,259,951 B1 | 7/2001 | Kuzma et al. | |
| 6,304,840 B1 | 10/2001 | Vance et al. | |
| 6,452,499 B1 | 9/2002 | Runge et al. | |
| 6,479,890 B1 | 11/2002 | Trieu et al. | |
| 6,575,020 B1 | 6/2003 | de Charmoy Grey et al. | |
| 6,631,638 B2 | 10/2003 | James et al. | |
| 6,825,539 B2 | 11/2004 | Tai et al. | |
| 6,826,960 B2 | 12/2004 | Schaad et al. | |
| 6,923,054 B2 | 8/2005 | Liu et al. | |
| 7,122,152 B2 | 10/2006 | Lewis et al. | |
| 7,135,852 B2 | 11/2006 | Renken et al. | |
| 7,150,195 B2 | 12/2006 | Jacobson | |
| 7,357,035 B2 | 4/2008 | Liu et al. | |
| 7,644,624 B2 * | 1/2010 | Liu et al. | 73/756 |
| 2002/0049080 A1 | 4/2002 | Thompson | |
| 2004/0142477 A1 | 7/2004 | Kumagai et al. | |
| 2007/0234793 A1 | 10/2007 | Liu | |
| 2008/0022513 A1 | 1/2008 | Liu | |
| 2008/0022778 A1 | 1/2008 | Liu | |
| 2008/0072682 A1 | 3/2008 | Liu | |
| 2008/0072683 A1 | 3/2008 | Liu | |
| 2008/0089383 A1 | 4/2008 | Liu | |

FOREIGN PATENT DOCUMENTS

| | | |
|---|---|---|
| WO | WO-03/021679 | 3/2003 |

OTHER PUBLICATIONS

J. Chen, J.M. Engel and C. Liu, "Development of polymer-based artificial haircell using surface micromachining and 3D assembly," presented at Transducers, Boston 2003.

Y. Ozaki, T. Ohyama, T. Yasuda and I. Shimoyama, "Air flow sensor modeled on wind receptor hairs of insects," presented at IEEE International Conference on MEMS, 2000.

K. Shida and J.I. Yuji, "Discrimination of Material Property by Pressure-Conductive Rubber Sheet Sensor with Multi-sensing Function," presented at IEEE International Symposium on Industrial Electronics, 1996.

J.M. Engel, J. Chen and C. Liu, "Development of a multi-modal, flexible tactile sensing skin using polymer micromachining," presented at the 12$^{th}$ International Conference on Solid-state Sensors, Actuators and Microsystems, Boston, MA, 2003.

Zou, J., Chen, J., Liu, C. & Schutt-Aine, J.E. "Plastic Deformation Magnetic Assembly (PDMA) of Out-of-Plane Microstructures: Technology and Application," Journal of Microelectromechanical Systems, 10, 302-309 (2001).

Chen, J. & Liu, C. "Development and characterization of surface micromachined, out-of-plane hot-wire anemometer." JMEMS 12, 979-88 (2003).

Ayers, J., Zavracky, P.M., McGruener, N., Massa, D., Vorus, V., Mukherjee, R., Currie, S., 1998, "A Modular Behavioral-Based Architecture for Biomimetic Autonomous Underwater Robots," Proc. Autonomous Vehicles in Mine Countermeasures Symp., Naval Postgraduate School, CD ROM, http://www.cix.plym.ac.uk/cis/InsectRobotics/Biomimetics.htm, pp. 1-18.

Barnes, T.G., Truong, T.Q., Lu, X., McGruer, E., Adams, G.G., "Design, Analysis, Fabrication, and Testing of a MEMS Flow Sensor," 1999 ASME International Congress and Exposition on MEMS, vol. 1, 1999, pp. 355-361.

Beebe, D.J., Hsieh, A.S., Denton, D.D., and Radwin, R.G., "A Silicon force Sensor for Robotics and Medicine," Sensors and Actuators, A 50, 1995, pp. 55-65.

Boillat, M.A., van der Wiel, A.J., Hoogerwerf, A.C., de Rooij, N.F., "A Differential Pressure Liquid Flow Sensor for Flow Regulation and dosing Systems," Proc. IEEE Micro Electro Mechanical Systems, 1995, pp. 350-352.

Chen, J., Fan, Z., Engel, J., Liu, C. "Towards Modular Integrated Sensors: The Developments of Artificial Haircell Sensors Using Efficient Fabrication Methods," Proc. of the 2003 IEEE/RSK Intl. Conf. on Intelligent Robots and Systems, Las Vegas, NV, Oct. 2003.

de Bree, H-H, Jansen, H.V., Lammerink, T.S.J., Krijnen, G.J.M,

Elwenspoek, m., 1999, "Bi-Directional Fast Flow Sensor with a Large Dynamic Range," J. Micromech. Microeng. 9 (1999), pp. 186-189.

Ebefors, T., Kalvesten, E., Stemme, G., "Three Dimensional Silicon Triple-Hot-Wire Anemometer Based on Polyimide Joints," Proc. 11$^{th}$ Annual Int. Workshop on Micro Electro Mechanical Systems: An Investigation of Micro Structures, Sensor, Actuators, Machines and Systems, Heidelberg, Germany, 1998, pp. 93-98.

Editor, "Touchy Touchy," The Economist, 2002, pp. 66-67.

Engel, J., Chen, J., Liu, C, "Development of Polyimide Flexible Tactile Sensor Skin," Journal of Micromechanics and Microengineering, vol. 13, No. 9, 2003, pp. 359-366.

Enoksson, P., Stemme, G., Stemme, E., "A Coriolis Mass Flow Sensor Structure in Silicon," Proc. 9$^{th}$ Annual Int. Workshop on Micro Electro Mechanical Systems: An Investigation of Micro Structures, Sensors, Actuators, Machines and Systems, 1996, pp. 156-161.

Gray, B.L., Fearing, R.S., "A Surface Micromachined Microtactile Sensor Array," Proc 1996 IEEE Int'l Conf. on Robotics and Automation, Minneapolis, MN, 1996, pp. 1-6.

Jiang, F., Tai, Y.C., Ho, C.M., Rainer, K., and Garstenauer, M., Theoretical and Experimental Studies of Micromachined Hot-Wire Anemometer, Digest IEEE Int. Electron Devices Meetings (IEDM) (San Francisco), 1994, pp. 139-142.

Jiang, F., Tai, Y.C., Walsh, K., Tsao, T., Lee, G.B., Ho, C.M., "A Flexible MEMS Technology and its First Application to Shear Stress Sensor Skin," Proc 1997 IEEE Int'l Conf. on MEMS, pp. 465-470.

Kalvesten E., Vieider C., Lofdahl, L., Stemme, G., "An Integrated Pressure-Flow Sensor for Correlation Measurements in Turbulent Gas Flows," Sensors Actuators A 52, 1996, pp. 51-58.

Kane, B.J., Cutkosky, M.R., Kovacs, T.A., "A Traction Stress Sensor Array for Use in High-Resolution Robotic Tactile Imaging," Journal of MEMS, vol. 9, 2000, pp. 425-434.

Kolesar, E.S., Dyson, C.S., "Object Imaging with a Piezoelectric Robotic Tactile Sensor," Journal of MEMS, vol. 4, No. 2, 1995, pp. 87-96.

Lee, M.H., Nicholls, H.R., "Tactile Sensing for Mechatronics—a State of the Art Survey," Mechatronics, vol. 9, 1999, pp. 1-33.

Leineweber, M., Pelz, G., Schmidt, M., Kappert, H., Zimmer, G., "New Tactile Sensor Chip with Silicone Rubber Cover," Sensors and Actuators vol. 84, 2000, pp. 236-245.

Liu et al., "Polymer Micromachining and Applications in Sensors, Microfluidics, and Nanotechnology," 226$^{th}$ American Chemical Society National Meeting, New York, 2002.

Liu, C., Huang, J., Zhu, Z., Jiang, F., Tung, S., Tai, Y.C., Ho, C.M., "A Micromachined Flow Shear-Stress Sensor Based on Thermal Transfer Principles," IEEE/ASME Journal of Microelectromechanical Systems (JMEMS), vol. 8, No. 1, 1999, pp. 90-99.

Lofdahl, L., Kalvesten, E., Hadzianagnostakis, T., Stemme, G., "An Integrated Silicon Based Wall Pressure-Shear Stress Sensor for Measurements in Turbulent Flows," DSC-vol. 59, Proc. 1996 Int. Mechanical Engineering Congress and Exposition, New York, NY, 1996, pp. 245-251.

Lofdahl, L., Stemme, E., Stemme, G., 2001, "Silicon Based Flow Sensors Used for Mean Velocity and Turbulence Measurements," Exp. in Fluids, 12, 1992, pp. 270-276.

Martin, R., "Mother Knows Best: Imitating Nature is the Sincerest Form of Flattery," Forbes ASAP, 2002, pp. 26-29.

Padmanabhan, A., Goldberg, H., Breuer, K.D., Schmidt, M.A., "A Wafer-Bonded Floating-Element Shear Stress Microsensor with Optical Position Sensing by Photodiodes," J. Microelectromech. Syst., vol. 5, No. 4, 1996, pp. 307-315.

Pfann, W.G., Thurston, R.N., "Semiconducting Stress Transducers Utilizing the Transverse and Shear Piezoresistance Effects," J. Appl., Phys. vol. 32, No. 10, 1961, pp. 2008-2009.

Reston, R.R., Kolesar, E.S., "Robotic Tactile Sensor Array Fabricated from a Piezoelectric Polyvinylidene Fluoride Film," Proc 1990 IEEE NAECON 3, pp. 1139-1144.

Richter, M., Wackerle, M., Woias, P., and Hillerich, B., 1999, "A Novel Flow Sensor with High Time Resolution Based on Differential Pressure Principle," Proc., 12 Int. Conf. on Micro Electro Mechanical Systems (Orlando, FL), pp. 118-123.

Shimizu, T., Shikida, M., Sato, K., Itoigawa, K., "A New Type of Tactile Sensor Detecting Contact Force and Hardness of an Object," Proc 2002 IEEE Int'l Conf. on MEMS, 2002, pp. 344-347.

Su et al., "Characterization of a Highly Sensitive Ultra-Thin Piezoresistive Silicon, Cantilever Probe and its Application in Gas Flow Velocity Sensing," Journal of Micromechanics and Microengineering, vol. 12, 2002, pp. 780-785.

Sugiyama, S., Kawahata, K., Yneda, M., Igarashi, I, "Tactile Image Detection Using a 1K-Element Silicon Pressure Sensor Array," Sensors and Actuators A21-A23, 1990, pp. 397-400.

Svedin, N., Kalvesten, E., Stemme, E., Stemme, G., "A New Silicon Gas-flow Sensor Based on Lift Force," J. Microelectromech. Syst., vol. 7, No. 3, 1998, pp. 303-308.

Svedin, N., Stemme, E., Stemme G., "A Static Turbine Flow Meter with a Micromachined Silicon Torque Sensor," Technical Digest MEMS 2001: 14$^{th}$ IEEE Int. Conf. on Micro Electro Mechanical Systems (Interlaken, Switzerland), 2001, pp. 208-211.

Thaysen et al., "Polymer-based Stress Sensor with Integrated Readout," Journal of Physics D—Applied Physics, vol. 35, No. 21, Nov. 2002, pp. 2698-2703.

van Baar, J.J., Wiegerink, R.J., Iammerink, T.S.J., Krijnen, G.J.M., Elwenspoek, M., "Micromachined Structures for Thermal Measurements of Fluid and Flow Parameters," J. Micromech. Micoeng., 11, 2001, pp. 311-318.

van der Wiel, A.J., Linder, C., Rooij de, N.F., Bezinge, A., 1993, "A Liquid Velocity Sensor Based on the Hot-Wire Principle," Sensors Actuators, A37-A38, pp. 693-697.

van Honschoten, J.W., Krijnen, G.J.M., Svetovoy, V.B., de Bree, H-E, Elwenspoek, M.C., 2001, "Optimization of a Two Wire Thermal Sensor for Flow and Sound Measurements," Proc. 14$^{th}$ Int. Conf. Micro Electro Mechanical Systems (MEMS' 2001), pp. 523-526.

Xu, Y., Jiang, F., Lin, Q., Clendenen, J., Tung, S., and Tai, Y.C., 2002, "Under Water Shear Stress Sensor," MEMS '02: 15$^{th}$ IEEE Int. Conf. on Micro Electro Mechanical Systems, Las Vegas, NV, 2002, pp. 340-343.

Chen, J., Fan, Z., Zou, J., Engel, J., Liu, C., "Two Dimensional Micromachined Flow Sensor Array for Fluid Mechanics Studies," ASCE Journal of Aerospace Engineering, Apr. 2003, pp. 85-97.

Fan, Z., Chen, J., Zou, J., Bullen, D., Liu, C., and Delcomyn, F., "Design and Fabrication of Artificial Lateral Line Flow Sensors," Journal of Micromechanics and Microengineering, 12 (2002), pp. 655-661.

Li, J., Fan, Z., Chen, J., Zou, J, Liu, C., "High Yield Microfabrication Process for Biomimetic Artificial Haircell Sensors," smart Electronics, MEMS, and Nanotechnology, Conference (Conference 4700), SPIE's 9th annual International Symposium on Smart Structures and Materials, Mar. 17-21, 2002, San Diego, CA.

Petersen, "Silicon as a Mechanical Material," Proc of the IEEE, vol. 70, No. 5, 1982, pp. 420-457.

Chen, J., Engel, J., Chen, N., Pandya, S., Coombs, S. and Liu, C., "Artificial Lateral Line and Hydrodynamic Object Tracking," presented at IEEE/ASME Conference on Microelectromechanical Systems, Istanbul, Turkey, May 2006.

Pandya, S., Yang, Y., Jones, D., Engel, J. and Liu, C., "Multisensor Processing Algorithms for Underwater Dipole Localization and Tracking using MEMS Artificial Lateral-Line Sensors," Micro and Nanotechnology Laboratory & Coordinated Science Laboratory, University of Illinois at Urbana-Champaign, EURASIP JASP, Jul. 2006.

Chen, J., Engel, J. Chen, N, and Liu, C., "A Monolithic Array of Out-of-Plane Hot-Wire Flow Sensors and Demonstration of Boundary-Layer Flow Imaging," presented at the 18$^{th}$ IEEE International Conference on Micro Electro Mechanical Systems, MEMS 2005, Miami Beach, FL, 2005.

* cited by examiner

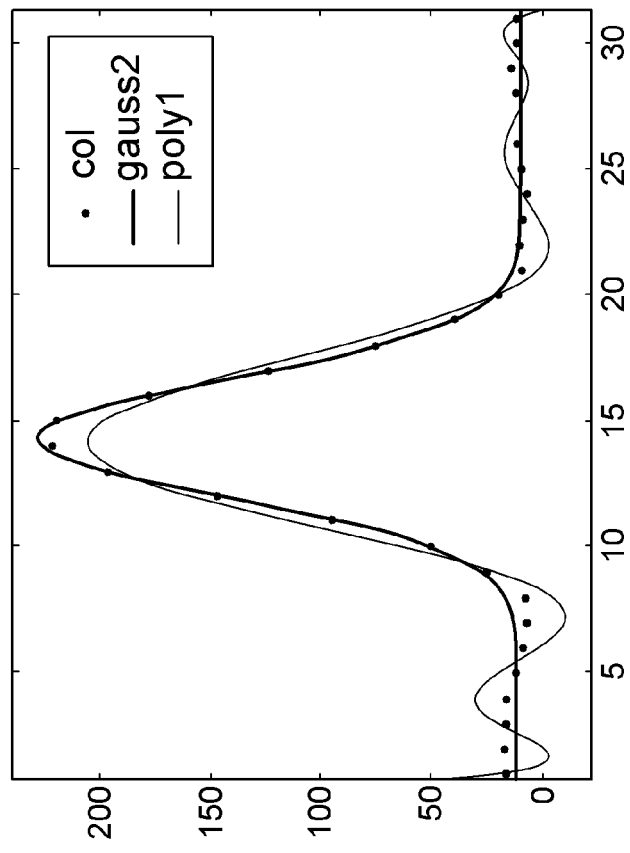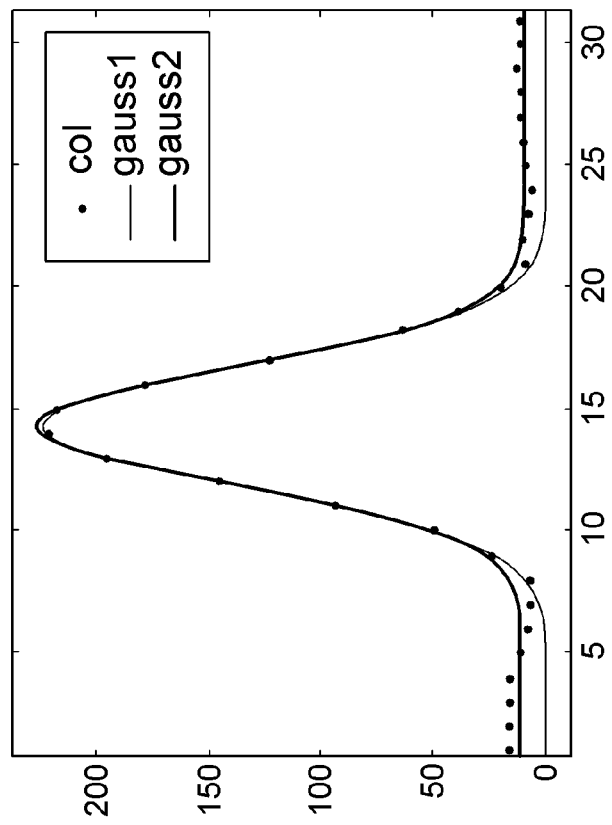
FIG. 13A
FIG. 13B

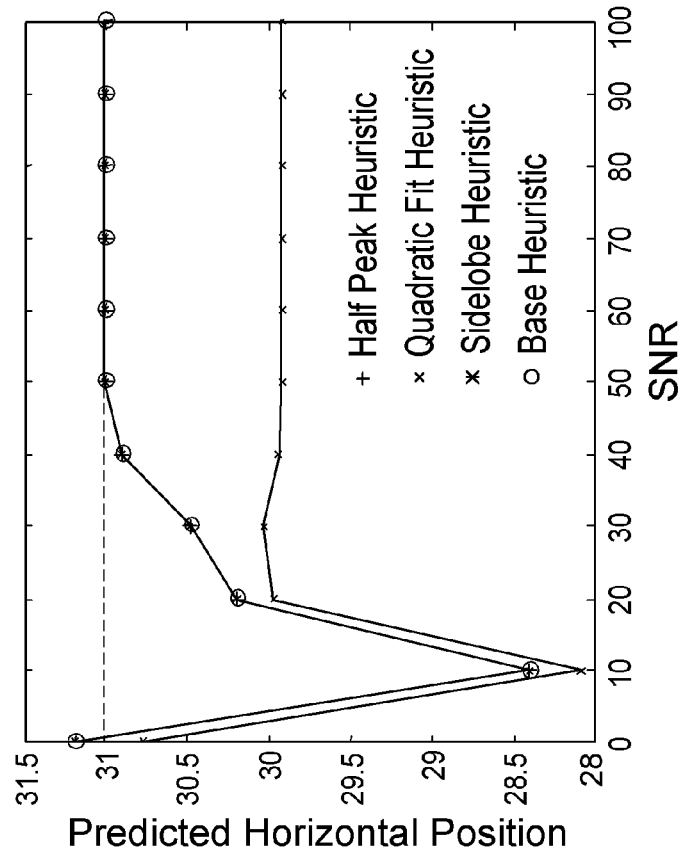
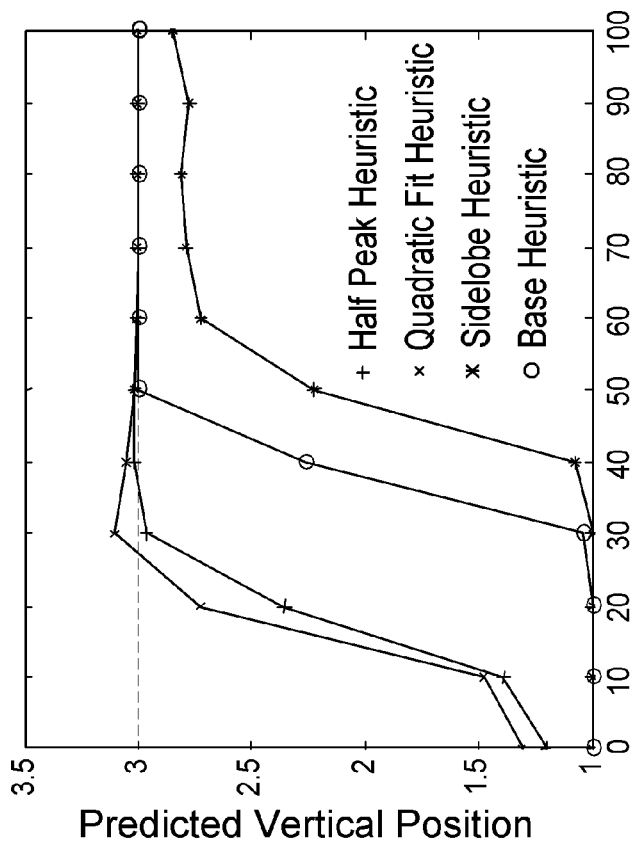
FIG. 20B
FIG. 20A

ARTIFICIAL LATERAL LINE

PRIORITY CLAIM

This application is a continuation of U.S. patent application Ser. No. 11/824,042, filed Jun. 29, 2007, now U.S. Pat. No. 7,644,624 which is a continuation-in-part of U.S. patent application Ser. No. 10/861,096, filed Jun. 4, 2004, now U.S. Pat. No. 7,357,035, issued Apr. 15, 2008. This application claims the benefit of U.S. Provisional Patent Application Ser. No. 60/817,885, filed Jun. 30, 2006, under 35 U.S.C. §119.

STATEMENT OF GOVERNMENT INTEREST

This invention was made with Government assistance under Air Force Office of Scientific Research (AFOSR) Grant No. FA9550-05-1-0459. The Government has certain rights in the invention.

FIELD OF THE INVENTION

This application relates generally to the field of artificial sensors.

BACKGROUND OF THE INVENTION

Comprehensive flow sensing involves measurement of, for example, pressure, shear stress (drag and vortex), temperature, and three-axis flow rates. The spatial and temporal evolution of surface flow features is extremely difficult to obtain due to limitations of convention scientific instruments. Conventional flow sensing instruments are singular point measurement devices only. Some prior devices have large sizes, and may change the characteristics of the flow.

Microfabricated flow sensing surfaces with one or more sensing modalities to provide spatial and temporal information would be extremely useful for experimental fluid mechanical studies and for underwater vehicles and platforms, for example. It is preferred that such sensors be fabricated using efficient, low-cost techniques, allow integration of signal processing units, and be mechanically robust.

SUMMARY OF THE INVENTION

An artificial sensor comprises at least one substrate, and a plurality of flow sensors disposed on the at least one substrate for providing a plurality of spatial-temporally varying signals representing a hydrodynamic stimulus. The plurality of flow sensors are spatially distributed on the at least one substrate. A processor is coupled to the plurality of flow sensors for receiving the signals and determining spatial-temporal information from the received signals.

BRIEF DESCRIPTION OF THE DRAWINGS

FIG. 13 shows a curve fitting comparison of MEMS sensor data with Gaussian curves, and curve fitting comparison of MEMS sensor data between candidate Gaussian and high order polynomial curves;

FIG. 20 shows performance of various heuristic localization models as a function of signal-to-noise ratio (SNR) in the vertical and horizontal direction;

DETAILED DESCRIPTION

Fish and many underwater animals utilize multimodal sensitive skin that can detect flow, pressure distribution, electrical potential and field, and local vortex. In nature, a lateral line is a spatially distributed system of flow sensors found on the body surface of fish and aquatic amphibians. A lateral line, for example, usually spans the length of the fish's body. Lateral lines form spatial-temporal images (AC, DC) of nearby sources based on the sources' hydrodynamic signatures.

Figure 1:
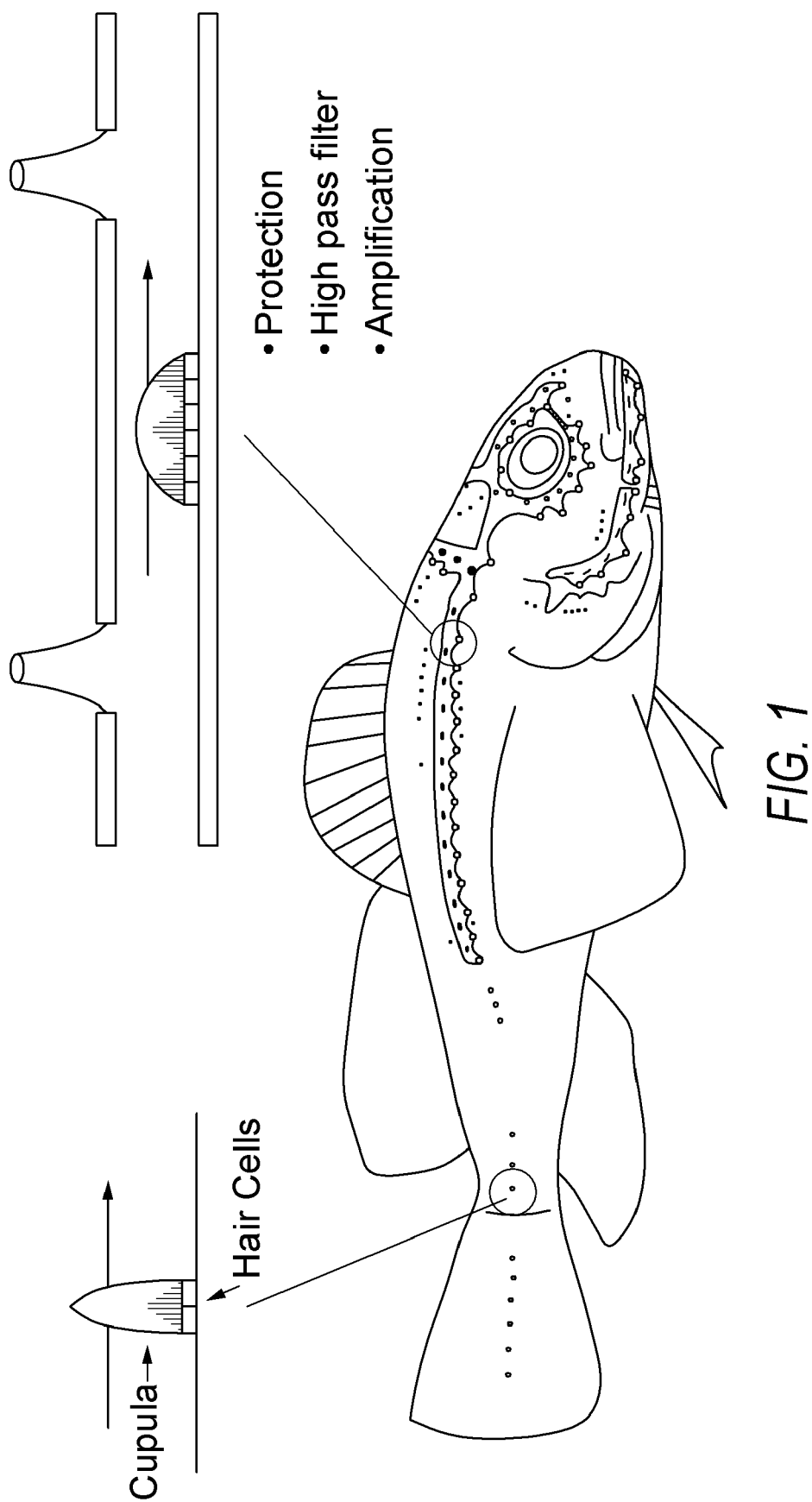
FIG. 1 is a prior art schematic representation of a fish lateral line.

For example, linearly distributed along the lateral line of fish are clustered sensor hair cell bundles embedded in a gel-like dome called neuromasts, each capable of sensing local flow velocity. Neuromasts can be classified into two types: superficial neuromasts, as shown in FIG. 1 (left), and canal neuromasts, as shown in FIG. 1 (right). A superficial neuromast is situated on the surface of the fish and responds in proportion to fluid velocity. By contrast, a canal neuromast is packaged in fluid-filled canals located beneath the surface of the skin. Canal neuromasts provide, for example, sensor protection, a high pass filter, and/or amplification. The bottom of FIG. 1 shows a lateral line periphery of a teleost fish. In FIG. 1, superficial neuromasts are represented by dots, while canal neuromasts are represented by dots inside shaded strips.

Water flowing past the neuromasts imparts forces to the hair cells and causes haircells to bend, with the extent of the bending determined by the speed of the flow. Individual cilia within a sensing node can sense flow rate. In certain species, the haircells lie outside of the epidermis. In others, they are embedded in sub-dermal canals for added protection against wearing and damages.

Exemplary lateral line functions include 1) detection of water flow around the fish body, allowing a fish to maintain stability within turbulent currents and 2) detection of distant objects such as obstacles, prey, and predators using direct or reflected waves. As an integrated flow sensing system, such lateral lines form spatial-temporal images of nearby sources based on their hydrodynamic signatures, and provide mechanosensory guidance for many different behaviors, including synchronized swimming in schools, predator and obstacle avoidance, prey detection and tracking, rhetoaxis, and holding station behind immersed obstacles in streams.

The lateral line, a "distant touch" sense, can complement other sensory modalities, such as vision or hearing, to increase survivability in unstructured environments. As non-limiting examples, a lateral line may be capable of responding to ocean currents, tidal streams, river flows, eddies, current distortions around stationary obstacles, currents generated by moving animals, predators, prey, mates, or moving body parts.

However, such functionalities conventionally have not been provided for artificial structures and/or devices. Thus, for example, underwater devices such as vehicles (e.g., submarines), robots, etc. are blind to hydrodynamic signals. This creates an absence of potentially vital information from use by such artificial structures and/or devices, and other types of sensing may not address this absence. Nearly all underwater vehicles and surface ships today use sonar and vision for imaging and navigation. Use of sonar, however, presents problems, both active and passive. Visual information may be severely lacking, for example, where vision is poor (e.g., in murky water).

Embodiments of the present invention provide, among other things, a micromachined artificial lateral line for generally mimicking the functional organization and imaging capabilities of the biological lateral line. This allows artificial structures including underwater structures to gather information that conventionally has not been provided. The example artificial lateral line allows a distant touch hydrodynamic imaging capability to critically augment sonar and vision systems, for example. Such an artificial lateral line is capable of significantly enhancing human ability to detect, navigate, and survive in an underwater environment.

Generally, an exemplary lateral line includes one or more sensors, preferably a plurality of sensors, spatially distributed along one or more substrates to provide hydrodynamic signals, in the form of electronic signal inputs, representing hydrodynamic stimulus. A single sensor may be used to provide temporal information, but it is preferred that a plurality of sensors be disposed along one or more substrates to provide spatial and temporal information (e.g., spatial-temporally varied signals). Plural sensors may be disposed on a substrate in a variety of ways, including but not limited to one- and two-dimensional arrays. Preferably, the sensors are monolithically integrated. A processor receives signals from the sensors and determines spatial-temporal information based on the signals.

An example artificial lateral line includes a monolithically integrated array of microfabricated flow sensors. Preferably, these flow sensors are sized and respectively spaced to approximate flow sensors for a biological counterpart lateral line.

The disposed sensors may be any of various types. One type of exemplary sensor includes hot-wire anemometers (HWA). An exemplary HWA includes a flow sensing element, such as a wire, elevated by two cantilevers (e.g., pillars), where the flow sensing element is made of a material such as, but not limited to, nickel. Another type of sensor includes artificial haircells. Mixed-mode sensors, including one or more of HWAs, haircells, and sensors for pressure, flow, chemical sensing, etc. may also be used. Generally, any type of flow sensor providing hydrodynamic signatures may be used. Preferred flow sensors are sensitive in multiple directions, and do not significantly interfere with movement (e.g., of an underwater vehicle or device on which the sensors are disposed). In certain embodiments, the sensors may be packaged or otherwise protected (e.g., waterproofed) or covered (e.g., by an artificial gel).

Further, sensors may be provided within artificial neuromasts. Such neuromasts may include, for example, a plurality of sensors providing a sensing node. The sensors in the sensing node may be, for example, arranged in an array. The sensing nodes may themselves be spatially distributed along one or more substrates.

One or more signal processors, and preferably a central processor, may be provided for native signal processing power. Processing algorithms may be provided for evaluating particular spatial and/or temporal inputs (e.g, hydrodynamic stimuli) and determining spatial-temporal patterns, such as hydrodynamic signatures, and/or providing temporal and/or spatial images. Signal conditioners, amplifiers, A/D or D/A converters, or other apparatus suitably coupled to the sensors and signal processors may be used to process, condition, and/or digitize inputs provided by the sensors. Algorithms may also be provided for making decisions based on such inputs, e.g., using a control loop to take action.

An example artificial lateral line can facilitate fundamental studies of biological systems, and provide unique sensing and control functions to underwater vehicles and platforms. Such a sensing system may be used for, as nonlimiting examples, imaging and maneuvering control for Autonomous Underwater Vehicles (AUV), Intrusion Detection (ID) systems, and hydro-robotics. For example, underwater vehicles and platforms equipped with example artificial lateral lines can detect intruders (e.g., a swimmer) based on the hydrodynamic signature, thereby allowing improved methods of threat monitoring.

Such lateral lines can, for example, augment existing artificial sensors, including but not limited to those providing sonar and vision capabilities.

Example applications for artificial lateral lines according to embodiments of the present invention are provided herein, including functions under biologically-relevant scenarios, such as localizing a moving target with a flapping part, and imaging a hydrodynamic trail for prey capture. However, it will be understood by those of ordinary skill in the art that lateral lines according to embodiments of the present invention are not limited to the specific example applications disclosed herein.

Figure 2A:
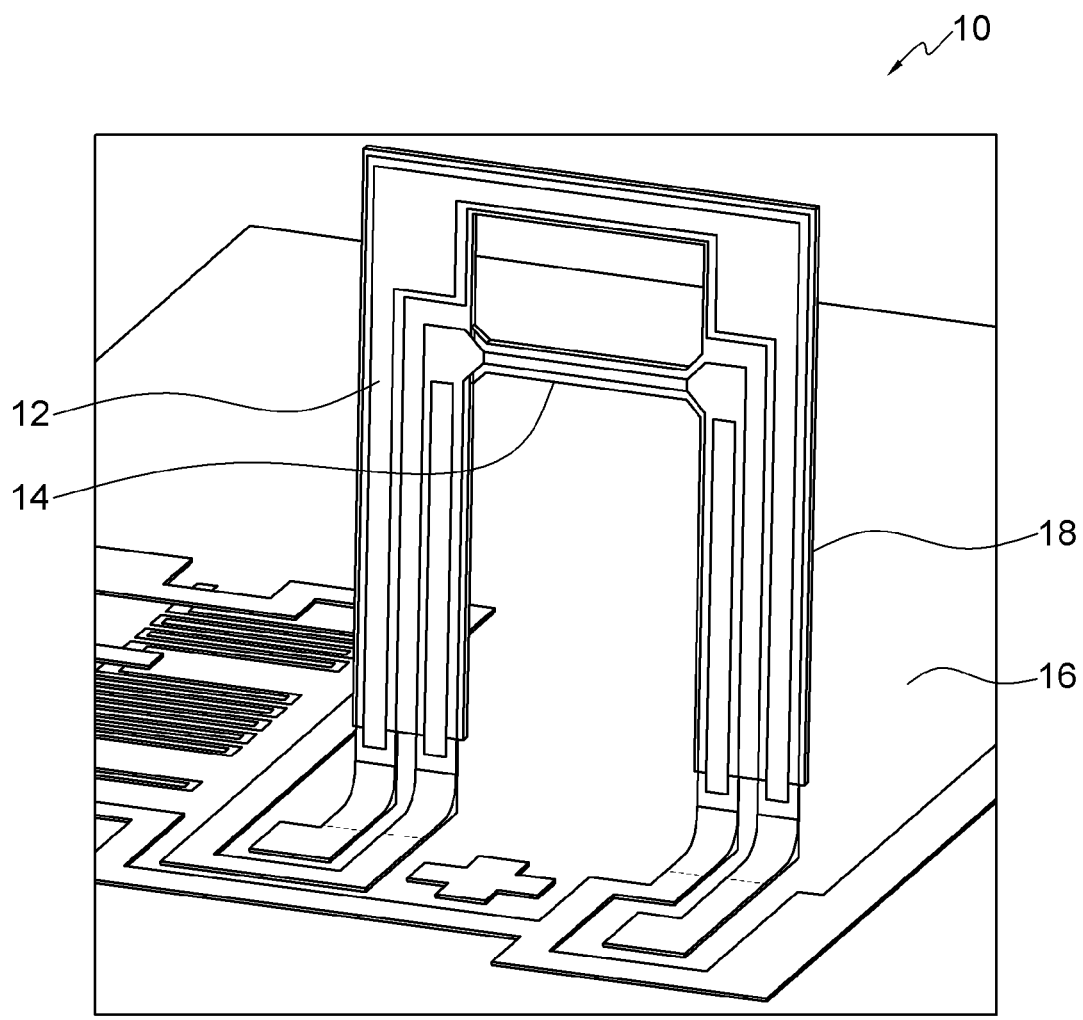
FIGS. 2A-2B show an individual, microfabricated anemometer, and an array of anemometers, respectively, according to an embodiment of the present invention.

Turning now to FIG. 2A, an example lateral line 10 includes a linear array of flow sensors 12, analogous to the array of neuromasts along the trunk of many fish. Individual flow sensors 12 may operate on various principles. The sizes of individual sensors and inter-sensor spacings are approximately 50 μm to 2 mm across biological species. The small dimensions of the sensors 12 are significant, as they ensure that they pose minimum interference with the flow field and with each other. Example artificial lateral lines 10 according to the present invention provide miniaturized sensors in dense arrays to provide similar benefits, and thus provide the capability to mimic the sizes and functions and organization of the lateral line. A processor coupled to the flow sensors receives the signals and determines spatial-temporal information from the received signals.

As a nonlimiting example, one or more, or all, of the individual sensors 12 may be based on a thermal hot wire anemometry (HWA) principle. Example sensors operating on this principle are disclosed in U.S. Pat. No. 6,923,054 and J. Chen and C. Liu, "Development and characterization of surface micromachined, out-of-plane hot-wire anemometer", JMEMS 12, 979-988 (2003). Hot wire anemometry sensors can exhibit high sensitivity and small dimensions, and consequently reduced interference to flow field. An individual HWA 12 includes a sensing element 14, such as a thermal resistive element (hot wire), suspended over a substrate 16, and operates on the principle of convective heat loss. During operation, the thermal resistive element 14 is heated above the ambient temperature using a current. When the element 14 is exposed to a flow media, the fluid flow convectively removes heat from the element and causes its temperature to drop and its resistance value to change. This provides a sensory input that can be used by example algorithms.

The hot wire 14 in the HWA 12 does not reside in the substrate plane (i.e., the bottom of the boundary layer) but rather is elevated above the substrate 16 by two prongs 18, just as some superficial neuromasts in fish are elevated above the skin surface by papillae. An example hot wire 12 includes a nickel filament that is sandwiched by two layers of polyimide, which serve as passivation and structural support. The polyimide layers provide passivation and structural support. An example nickel hot wire exhibits a temperature coefficient of resistance (α) of 4,100 ppm/° C.

Figure 2B:
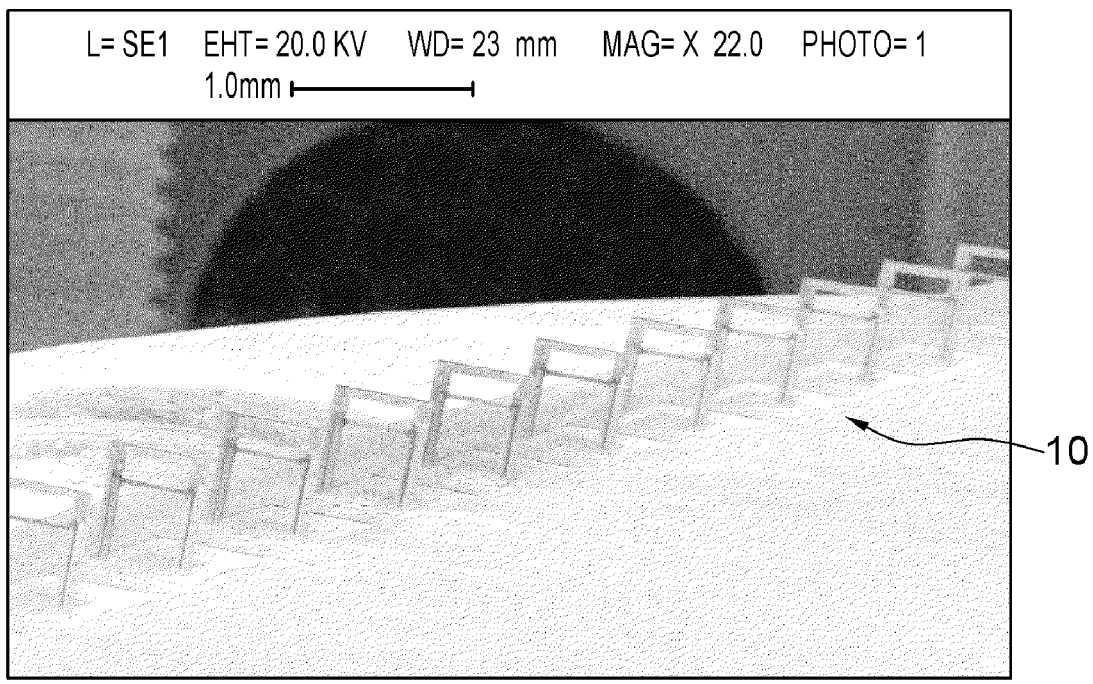
Figure 3A:
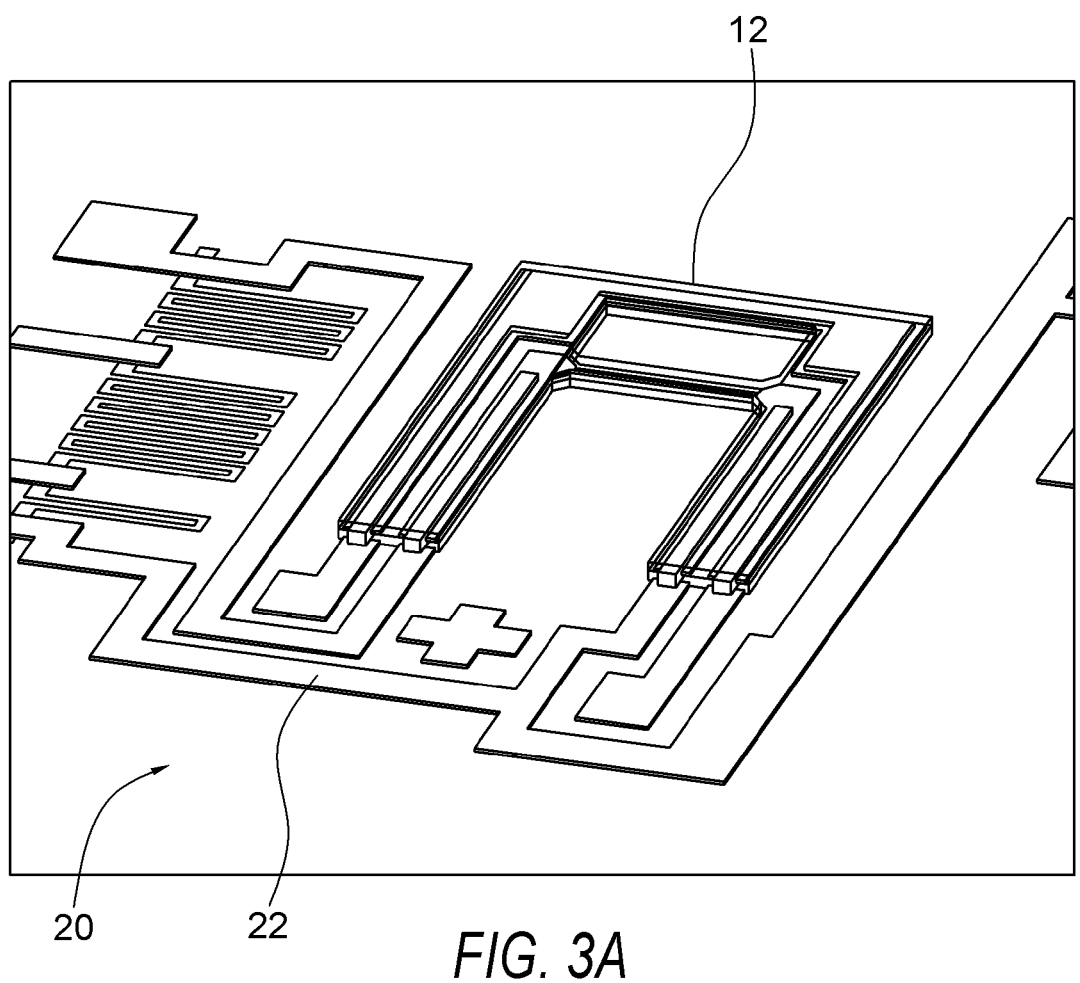
FIGS. 3A-3C show, respectively, an anemometer fabricated on a substrate, the anemometer raised from the substrate, and an array of anemometers.
Figure 3B:
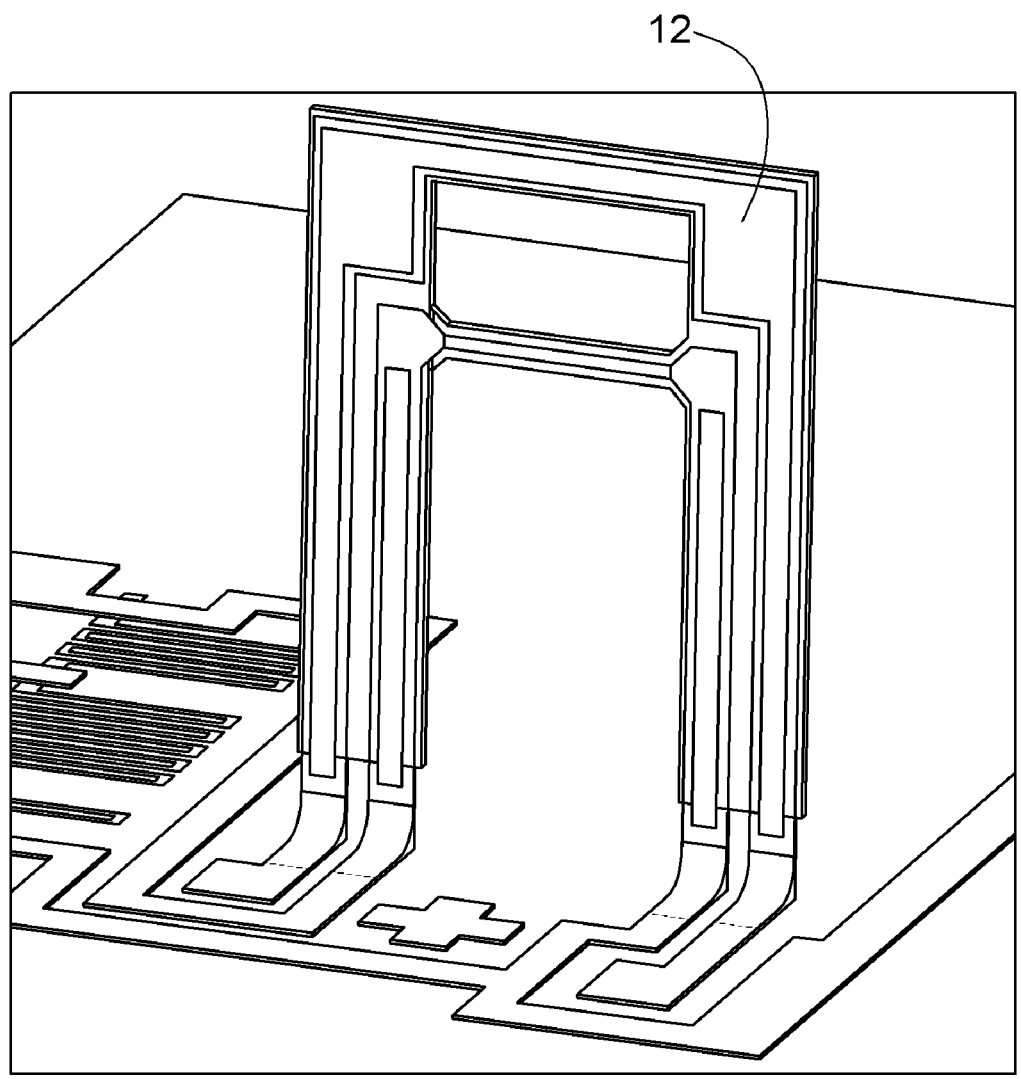

An example process, shown in FIGS. 3A-3B to fabricate arrays of miniature hot wire anemometers 12 shown in FIG. 2B uses surface micromachining, a technique commonly used in microelectromechanical systems (MEMS) to create free-standing cantilevers. The example process is performed on a silicon wafer 20 (FIG. 3A) with preexisting analog integrated circuitry 22. Surface micromachining is used to define the HWA 12, including a nickel-iron alloy support prong 18, and a nickel-polymer composite hot-wire sensing element 14. The resultant elevation corresponds to the design length of the prongs defined by photolithography.

The planar surface micromachining process is followed by a magnetically-assisted assembly step (FIG. 3B) that rotates the cantilevers out-of-plane. Using an example process for assembling the flow sensors out-of-plane, plastic deformation magnetic assembly (PDMA), as described by example in J. Zou, J. Chen, C. Liu, and J. E. Schutt-Aine, "Plastic Deformation Magnetic Assembly (PDMA) of Out-of-Plane Microstructures: Technology and Application", Journal of Microelectromechanical Systems, 10, 302-309 (2001), many devices can be bent out-of-plane in parallel with high yield. Further, the sensor elements can be monolithically integrated with signal processing electronics, as the example process is performed at room temperature and would not cause incompatibility with elements of electronic circuits. Generally, in PDMA, a magnetic material is formed on a portion of the cantilevers, and an external magnetic field is applied to induce plastic deformation in a region of the sensor. At the end of the process, the hot wire 14 may be encapsulated by a conformally deposited, 2 μm thick Parylene film for waterproofing and further structure strengthening.

An example lateral line 10 includes an array of miniature HWAs 12 having dimensions on the same order of magnitude (e.g., tens to hundreds of microns tall) as biological neuromasts. The elevation over the substrate 16 corresponds to the design length of the prongs defined by the photolithography process. If photolithography is used, micromachined HWA sensors 12 can have an example prong length, for example, from 50 μm up to 2 mm. An example HWA has a wire length of 400 μm and an elevation of approximately 600 μm.

Figure 3C:
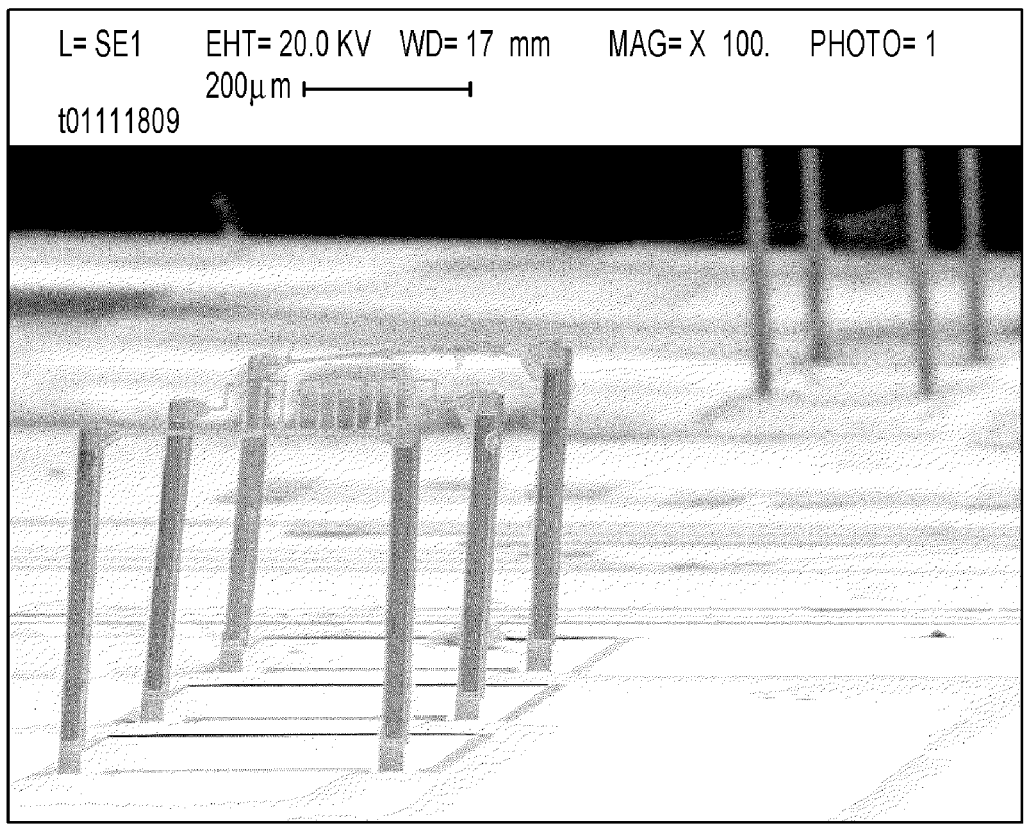

FIGS. 2B and 3C show an example array of HWA sensors providing a lateral line sensor. An example of a large array, the array includes 16 HWA sensors with 1 mm spacing. Each sensor is monolithically integrated with dedicated CMOS circuitry for on-chip signal conditioning, noise-floor reduction, and parallel data acquisition. Examples of such circuitry will be appreciated by those of ordinary skill in the art. A processor used to determine spatial-temporal information may be integrated with the chip or otherwise suitably coupled to the chip. Measurements for velocity sensitivities of individual sensors (characterized by moving the array in quiescent water at various speeds) indicate example thresholds of 200 μm/s and a bandwidth of 1 KHz.

Another example sensor type that may be used as a flow sensor for an artificial lateral line is an artificial haircell. Nonlimiting examples of artificial haircell flow sensors are provided in U.S. patent application Ser. No. 10/861,096, filed Jun. 4, 2004. Example artificial haircells are also described in J. Chen, Z. Fan, J. Engel, and C. Liu, "Towards Modular Integrated Sensors The Development of Artificial Haircell Sensors Using Efficient Fabrication Methods", Proceedings of the 2003 IEEE/RSJ Intl. Conference on Intelligent Robots and Systems, Las Vegas, Nev., October 2003; and J. Engel, J. Chen, D. Bullen, and C. Liu, "Polyurethane Rubber as a MEMS Material: Characterization and Demonstration of an All-Polymer Two-Axis Artificial Haircell Flow Sensor," 18$^{th}$ IEEE International Conference on Micro Electro Mechanical Systems, MEMS 2005, Miami Beach, Fla. USA, January 2005.

Another example artificial haircell 30, described in U.S. patent application Ser. No. 11/809,523, filed Jun. 1, 2007, and shown in FIG. 4, includes a high-aspect ratio (e.g., greater than 1:1) and tall (e.g., at or above 20 microns) cilia-like structure 32, i.e., a cilia-like artificial hair, attached to a movable support 34. The hair 32 is positioned generally out-of-plane of the support 34 so that it can receive a force from any of a variety of sources and displace in response to the force. Preferably, the hair 22 is made from a polymer material.

In operation, displacement of the hair 22 couples the force to the movable support 34, and in turn causes movement in the support. A strain detector 36 is provided on the support 34 to sense displacement of the support. Preferably, the strain detector 36 includes one or more piezoresistors formed by doping all of part of the support 34. Resistors 40, such as Wheatstone bridge resistors, are coupled to the strain detector. Such artificial haircells 30 may provide improved directional performance, robustness, and/or velocity sensitivity.

Figure 5:
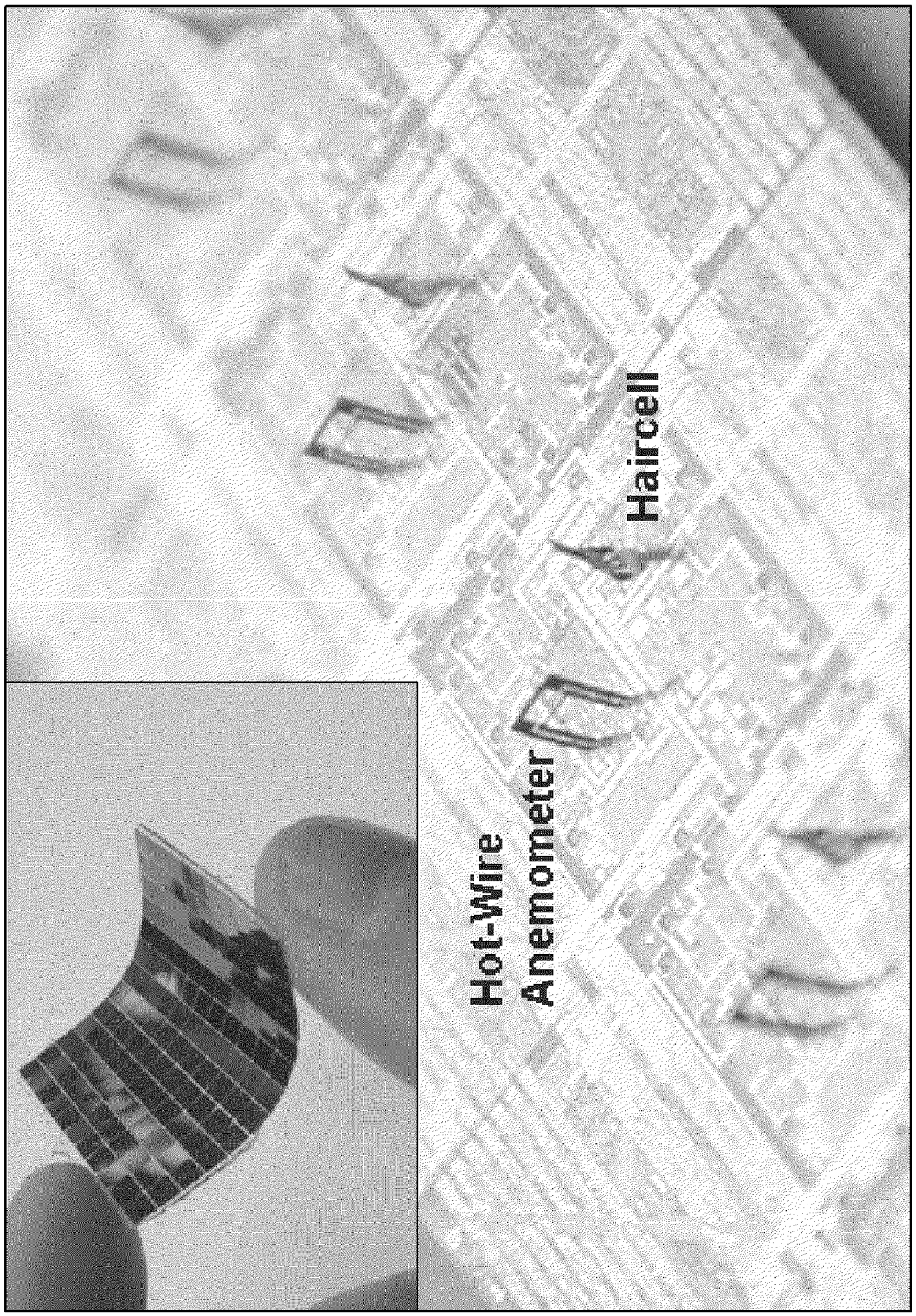
FIG. 5 shows a multimodal array of sensors disposed on a substrate.

Multimodal sensing arrays are also possible, as shown by example in FIG. 5, in which an array of HWA and an array of artificial haircells are disposed on a substrate. The arrangement, number, type, etc. of the flow sensors disposed on the substrate can vary as desired.

Figure 6:
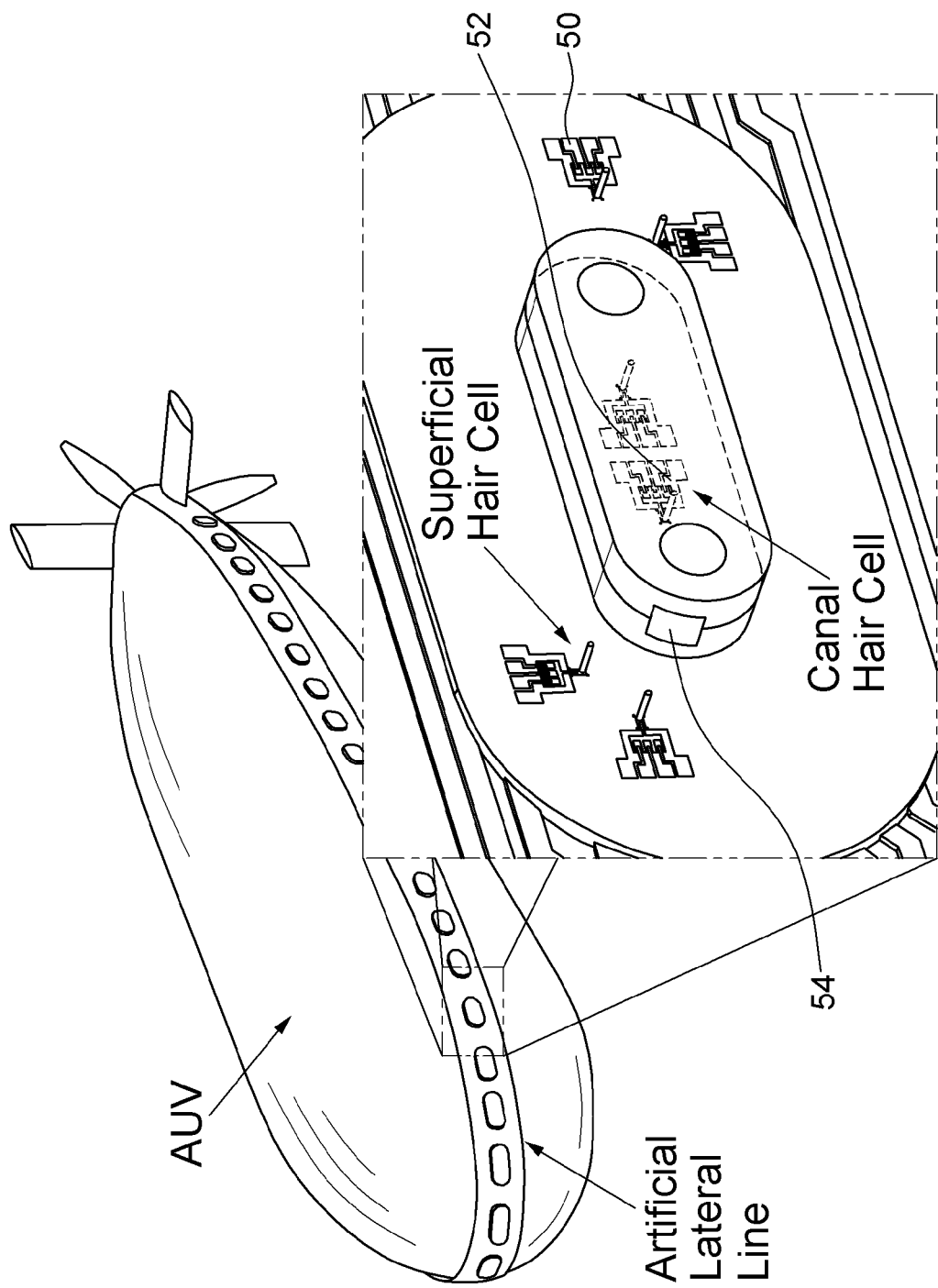
FIG. 6 shows a superficial sensor and a canal sensor.
Figure 7:
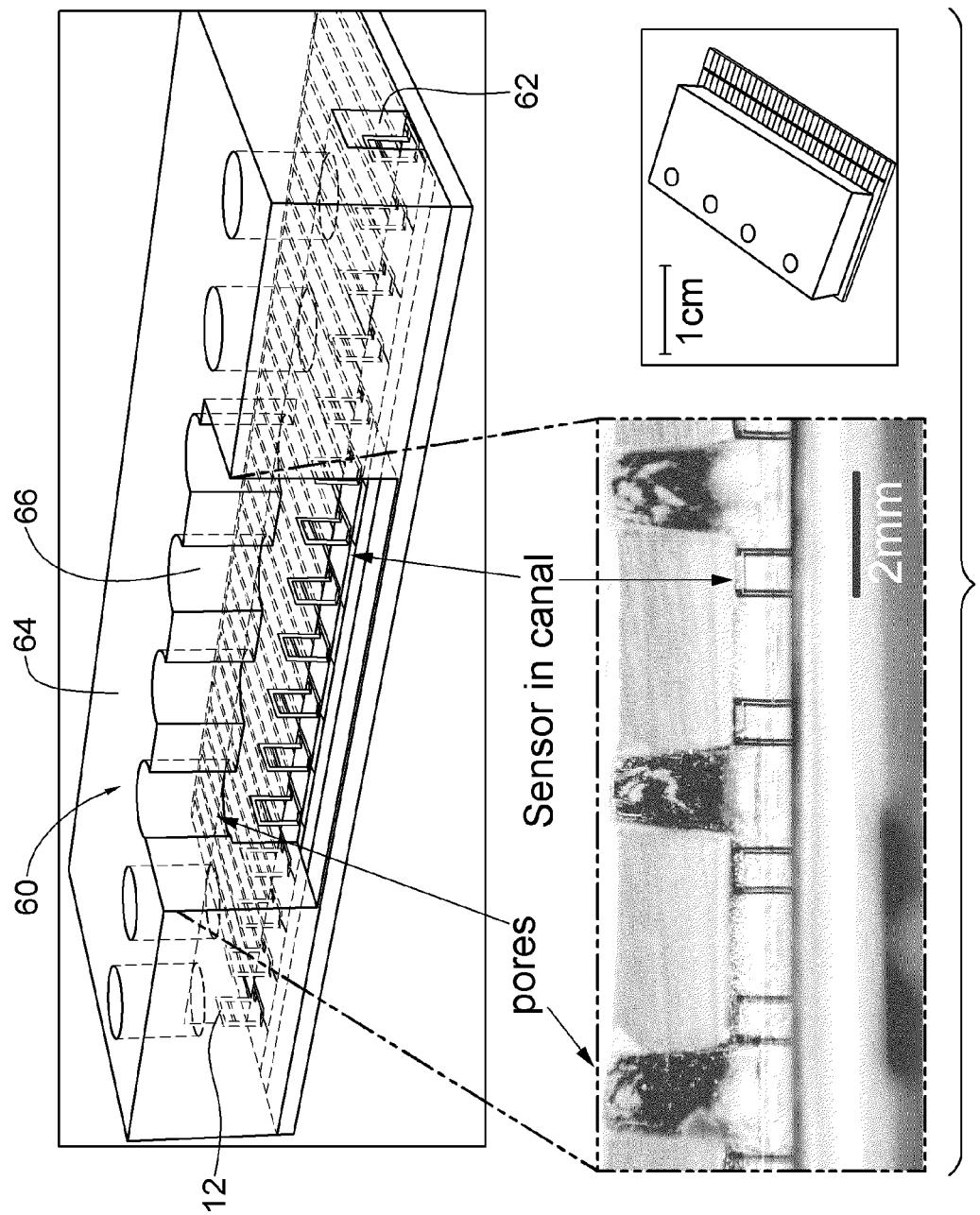
FIG. 7 shows a canal neuromast having an array of anemometers.

Similar to lateral lines for fish, a sensor in an example lateral line may be disposed as a superficial sensor 50 or as a canal sensor 52, as shown in FIG. 6, in which the substrate is covered by a suitable covering 54. A canal sensor 60 with HWA sensors 12 is shown in FIG. 7. A canal 62, such as a polymer or gel, is formed within a covering 64, and the array of sensors 12 is disposed within the canal. Pores 66 may extend from a surface of the covering 62 to the canal for allowing fluid flow.

Figure 4B:
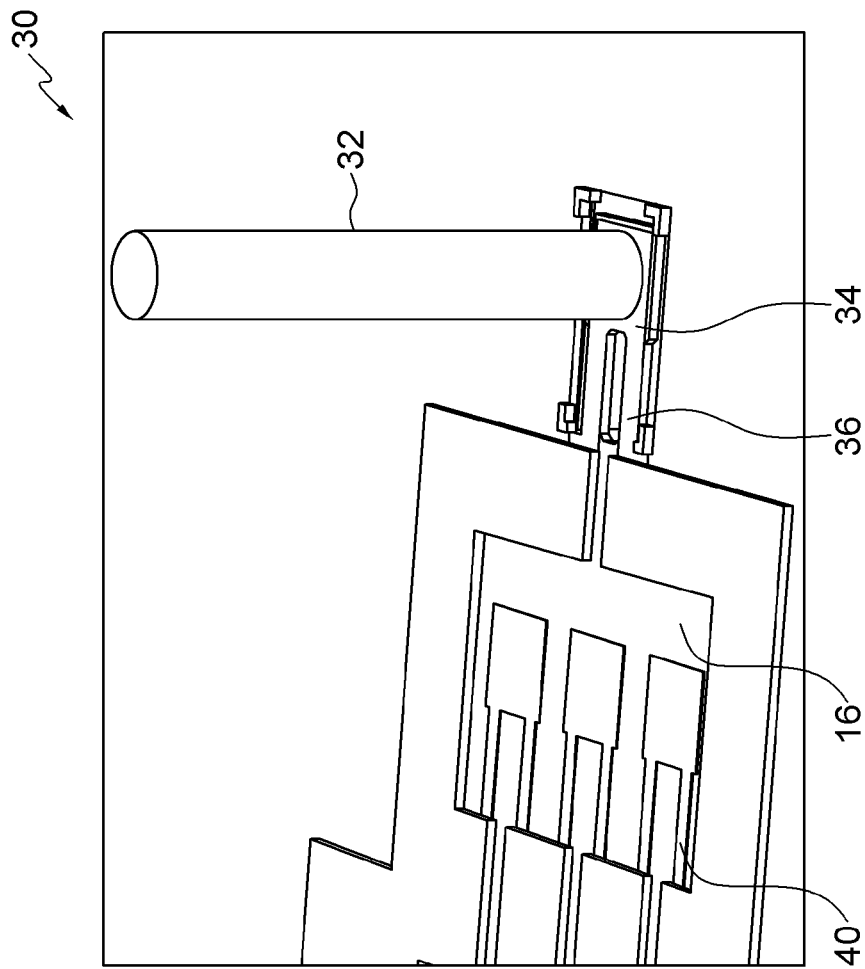
FIG. 4 shows an artificial haircell, according to an embodiment of the present invention.
Figure 4A:
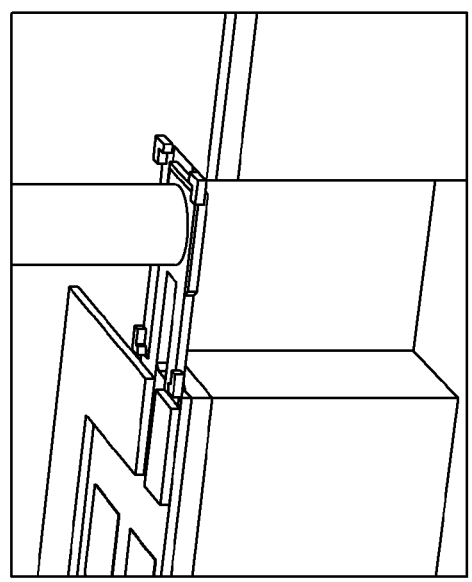
Figure 8:
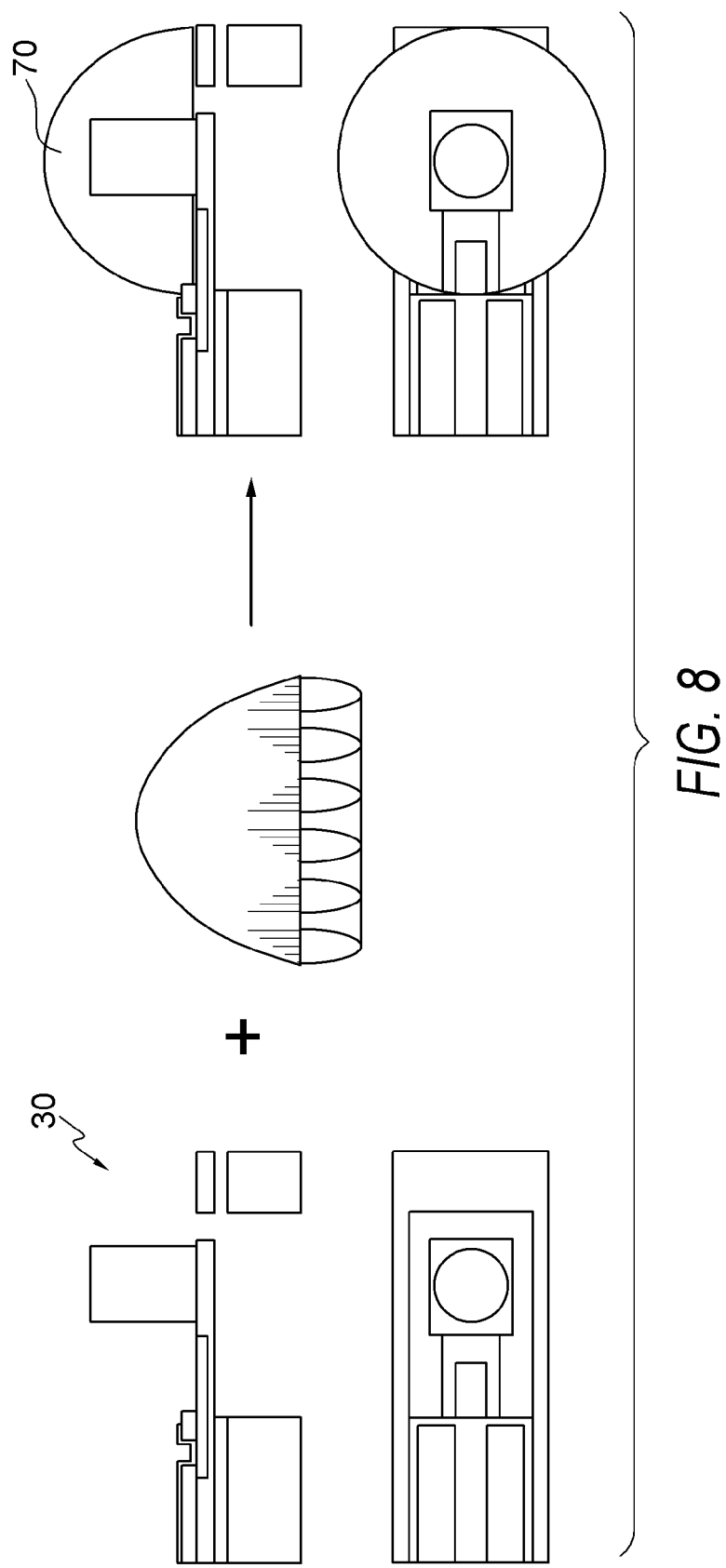
FIG. 8 shows an artificial haircell, and the haircell covered with a cupula.
Figure 9:
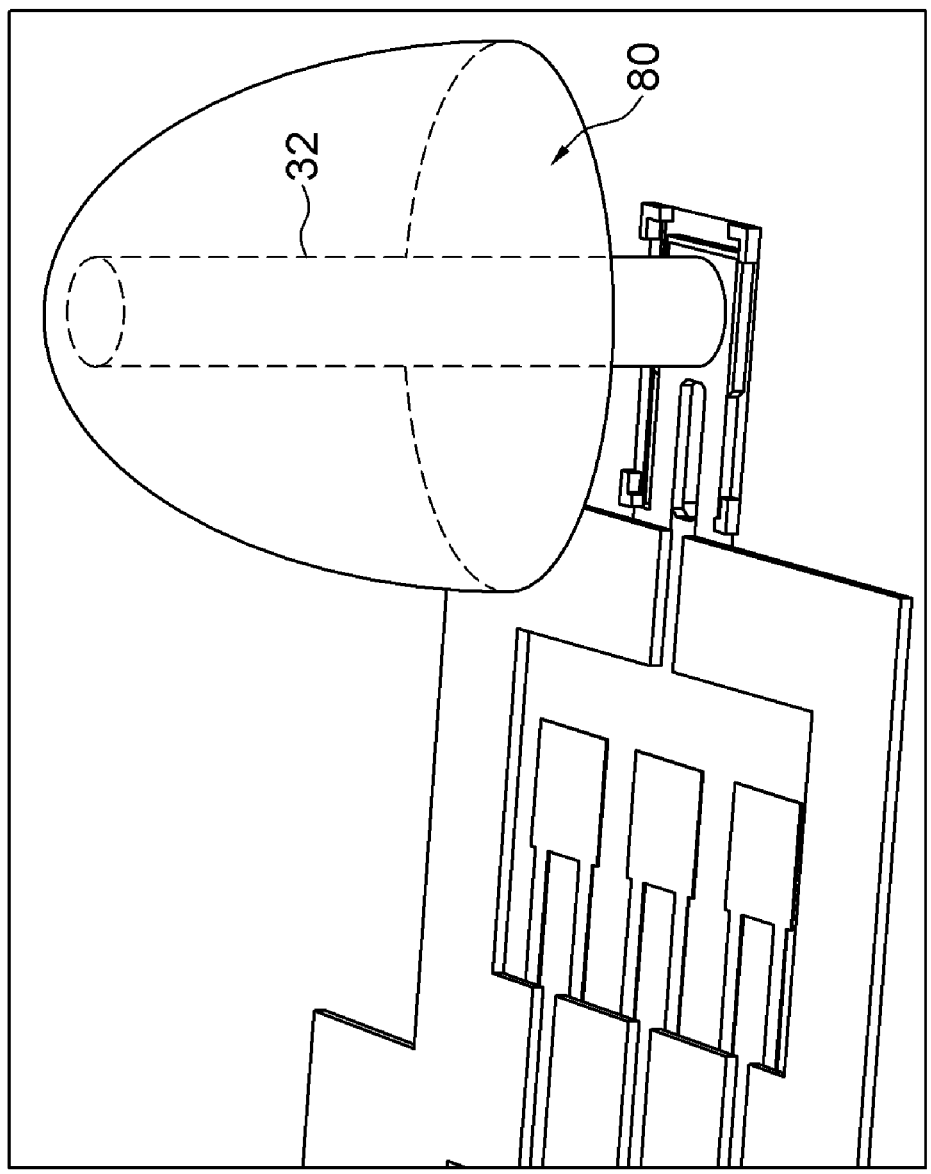
FIG. 9 shows an alternative cupula.

FIG. 8 shows an example hydrogel cupula covering 70 for a flow sensor, particularly the artificial haircell 30 shown in FIG. 4. FIG. 9 shows an alternative hydrogel cupula 80 assembled to a hair 32 to increase sensor sensitivity. A multi-material hair, e.g., a rubber base with SU-8 hair shaft, may be used to improve device robustness. The size, shape, and orientation of cupulae may vary widely, depending on, for example, whether they cover canal or superficial neuromasts, the width of the canal or location on the body surface, the size and shape of the underlying neuromast, and/or the orientation of the underlying sensor(s). Canal neuromasts cupulae, for example, may have small aspect ratios, e.g., almost as wide (or long) as they are tall. Superficial neuromast cupulae may have higher aspect ratios, e.g., greater than 4. Example lengths are between 30-300 μm. The area of the cupula base typically approximates that of the underlying neuromast, which is generally proportional to the number of sensors. For example, canal neuromasts are generally much larger with many more sensors than superficial neuromasts. Example diameters vary from less than 100 μm (superficial neuromasts) to between 200-1000 μm (canal neuromasts).

Example artificial lateral lines according to embodiments of the present invention have been used for hydrodynamic testing under biologically relevant scenarios. In exemplary methods, we have established the performance and functionality of an example artificial lateral line by recording the spatial-temporal response to a nearby dipole source. The dipole is simple and yet ubiquitous in the underwater world. For example, when a fish swims, its tail causes a dipolar near-field flow in addition to a wake behind it. It has been found that certain predators can accurately localize and attack a prey that is nearby (e.g., at a distance equivalent to one or two fish body lengths away) solely by using its lateral line system to measure the dipole field associated with the prey.

Inspired by fish behaviors, the spatially-distributed response from the example lateral line array can be used to identify the exact location of a moving dipole source. Example algorithms are provided according to embodiments of the present invention to assist in localization and tracking of vibrational dipole sources underwater. Using such algorithms allows accurate tracking of the trajectory of a moving dipole source.

The location of a dipole source is encoded in the location and amplitude of the apex. According to embodiments of the invention, example signal-processing algorithms are provided based on maximum likelihood analysis. Example algorithms compare the pattern of the signal received by the array with the expected pattern at all positions, and it selects the best match as the estimate of the actual dipole location. Particular example algorithms can predict the location of the dipole even when the apex lies outside of the length of the lateral line.

With an artificial lateral line including micromachined, e.g., MEMS, sensors, such as but not limited to the example 16-element array 10 of finely spaced hot-wire flow sensors 12, fast, efficient, and robust algorithms can be used to analyze complex spatial-temporal input from the sensor array for perception of hydrodynamic activities. According to embodiments of the present invention, algorithms are provided that complement a sensor such as the example artificial lateral line system 10 for a complete biomimetic hardware-software solution.

The density of the example HWA sensor 12 offers high performance in terms of sensitivity. For example, a fabricated MEMS HWA can sense flow on the order of 10 mm/sec. Such a sensor also provides a desired frequency range. Most hydrodynamic dipoles oscillate at low frequencies (<500 Hz). An example micromachined HWA has a viable frequency range from 0 (DC) to ~10 kHz, thus spanning the entire frequency range for hydrodynamic events of interest.

Pressure and velocity distributions, respectively, can be described according to an abridged version of an acoustic dipole model as:

$$p(r, \theta) = -\frac{\rho \omega a^3 U_0 \cos(\theta)}{2r^2} \quad (1)$$

$$v_{flow}(r, \theta) = \left(a^3 U_0 \frac{\cos(\theta)}{r^3}\right)\hat{e}_r + \left(\frac{a^3 U_0}{2r} \frac{\sin(\theta)}{r^3}\right)\hat{e}_\theta \quad (2)$$

Figure 10:
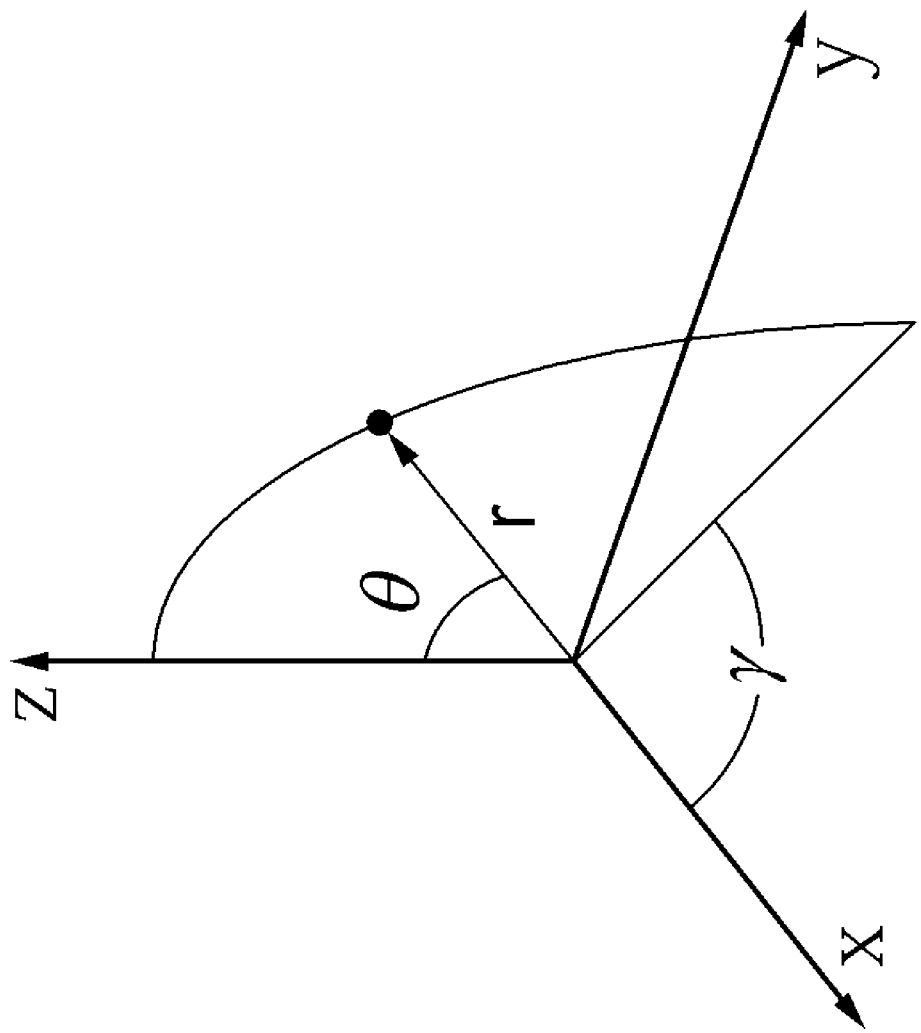
FIG. 10 shows an analytical model having a dipole at the origin and an observation point at $(r, \theta, \gamma)$.

Equation 1 relates the scalar pressure field of a dipole in the local flow region to the dipole diameter a, the density ρ, the observation distance r and angle θ, the angular frequency ω, as well as the dipole's initial vibrational velocity amplitude $U_0$. Equation 2 describes the local fluid flow velocity (vector field) as a function of the initial velocity, position, and dipole diameter. The position of the observation point, as well as the coordinate description, is shown in FIG. 10.

Figure 11B:
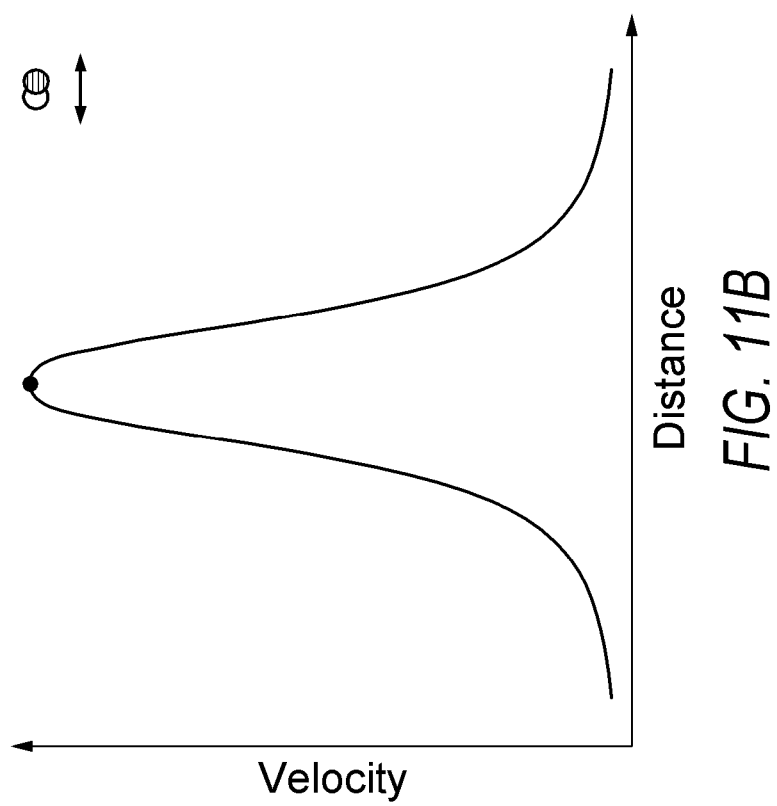
FIGS. 11A-B show velocity distribution in response to a dipole (shown as a filled-in circle) as a function of distance away from the dipole, and velocity distribution of a HWA response to a dipole (shown as a filled-in circle) as a function of distance away from the dipole.
Figure 11A:
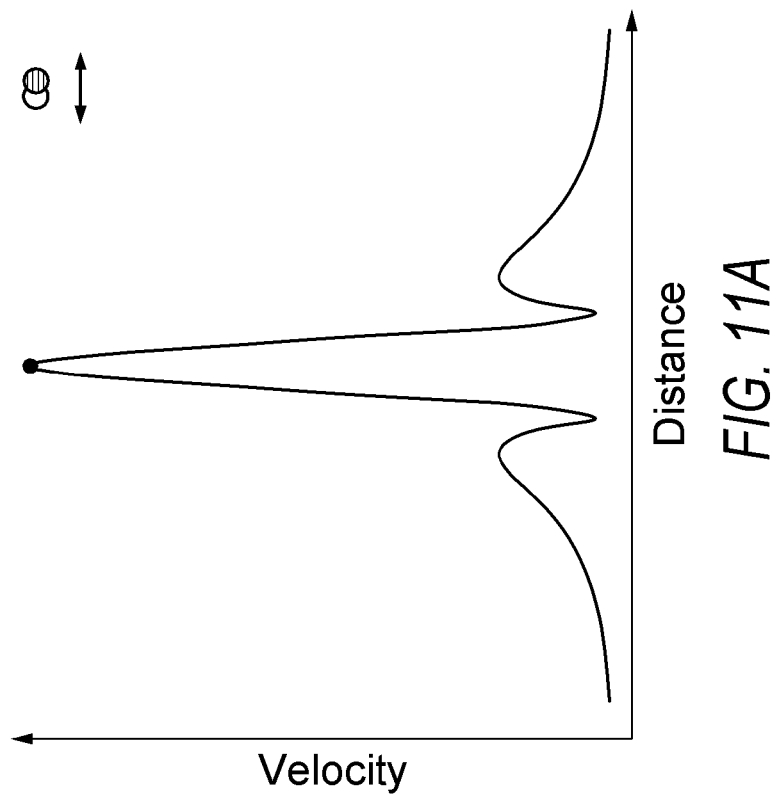

The spatial distribution of the magnitude of vibratory flow velocity in response to an oscillating dipole, as predicted by Equations 1-2, is shown in FIG. 11 (left) as a function of distance away from the dipole. FIG. 11 (right) shows the experimental response of an exemplary HWA to a dipole stimulus as a function of distance away from the dipole. In FIG. 11, the oscillating direction of the dipole is shown, and the dipole is shown as a filled-in circle. In both cases, the axis of the dipole course oscillation is parallel to the longitudinal axis of the lateral line. The experimental output of the HWA sensor matches pertinent profile information predicted by the theoretical model, such as the peak and the slope of the main lobe. The peak of the center lobe always coincides with the projected center of the oscillating dipole on the lateral line. As the distance between the oscillating dipole and the lateral line increases, the magnitude of the center lobe decreases and the width of the center lobe increases. The difference between the two profiles, noticeably the side lobe regions, can be attributed to the direction sensitivity of the HWA sensor.

Examples of signal processing algorithms are provided according to embodiments of the present invention, which can be used to predict a location of a dipole. Example algorithms are based on a template training approach, a modeling approach, and/or a heuristic approach. These example approaches operate on empirical data that is collected by the sensor array. Example algorithms based on these three approaches have been evaluated for accuracy, computational complexity, and ease of implementation. A description of each approach now follows.

The template training approach relies on a simple template-training method whereby an algorithm uses a template as a model and then compares the collected raw data to the template to make a decision. Within this approach, two sub-categories arise. Training can be done with the raw data or with a model developed from the raw data (a modeling approach). In example template training and modeling methods, a minimum mean squared error (MMSE) algorithm is used. It has been shown that, for independent, identically distributed Gaussian noise at each sensor (a reasonable assumption for electronic noise), this is also a maximum likelihood estimator (MLE).

Figure 12:
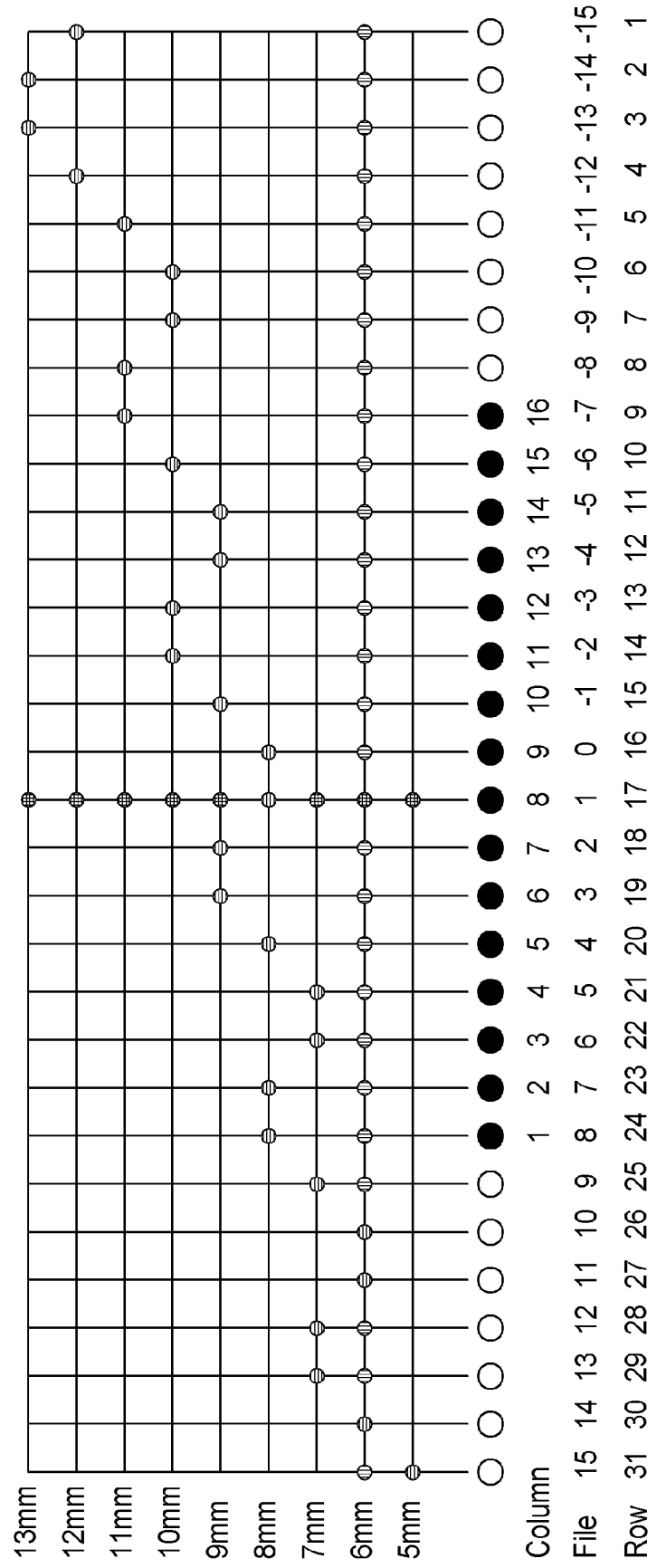
FIG. 12 shows an example training grid for recording template and experimental data.

In an example method for training with raw data, two data sets were collected and used. The first data set was called the training data set. The second data set was called the experimental data set. Systematic measurements were made, including dipole measurements taken at each vertex in a grid scanning two body-lengths of the sensor array along its axis and one body-length away from it, as shown in FIG. 12. Distance away from the array (normal to the array) was designated as the y-axis, whereas distance along (parallel to) the array was designated as the x-axis. Spatial distribution of the magnitude of flow velocity fluctuation was collected from the lateral line for the dipole source located at each grid point (vertex), with individual grid points 1 mm apart, as shown in FIG. 12. In an experiment, four dipole measurements were taken at each fixed position, i.e., at each specified grid point. These four measurements were averaged, and the averaged value was recorded at each grid point (vertex). A matrix of these averaged values formed the training data set.

In the second data set (experimental data set), experimental runs were recorded as the dipole source was mechanically swept along various paths or patterns. In FIG. 12, the y-axis is the distance away from the sensor array, represented by filled-in circles at the bottom. The x-axis is the distance along (parallel to) the sensor array. Of the experimental data sets, one experimental data set is along the x-axis (horizontal sweep), another is along the y-axis (vertical sweep), and the third was a composite step-curve.

For each integer position on the y-axis (within the relevant scope), a training matrix was created with rows being the horizontal integer positions (31 positions along the array) and with columns being the sensor outputs (16 sensors) averaged over four dipole measurement runs. Effectively, there were 9 positions (5-13 mm inclusive) vertically, leading to 9 training matrices. These were coalesced into a combined three-dimensional matrix, indexed by vertical position first, called the training data set as mentioned above. Each of the experimental data sets included an m by n matrix, where m is the number of experimental positions, and n is the number of sensor outputs.

A minimum mean squared error (MMSE) estimator was used as the principal algorithm for the template training and modeling approaches. We assume that we have a calibrated data training set, such as the created data set described above, to be used as a template. We also are assumed to have an experimental data set. Generally, for a set of sensor readings corresponding to a particular position (k) in the experimental data set, a search is performed through the template x-y grid. When the error between the experimental data set under consideration and a particular template is minimal, the x and y coordinates corresponding to that template constitutes the predictive solution. The example algorithm is presented in pseudo-code below, where A is a correlation factor between the template and data sets for the MMSE algorithm, $\epsilon$ is the error, and S is the predictive solution.

Let:
x be the distance along the array
y be the distance away from the array
s(x,y) be the position of the dipole relative to the array
d be the experimental data set with k positions of the dipole
t be the template data set
$S_{optimal}$(x,y) be the predicted position of the dipole
$\epsilon$ be the error
for X = 1 to x, (horizontal search space) {
    for Y = 1 to y, (vertical search space) {

$$A = \frac{t_{x,y,k} \cdot d^T}{t_{x,y,k} \cdot t_{x,y,k}^T}$$

$$\varepsilon = \sum_1^N (A \cdot t_{x,y,k} - d)^2$$

if ($\epsilon$ < minimumerror)
            minimumerror = $\epsilon$ } }
$S_{optimal,k} = \min_{x,y}(\epsilon)$ In another example method, a maximum projection algorithm is provided as follows:

Let:
x be the distance along the array
y be the distance away from the array
s(x,y) be the position of the dipole relative to the array
d be the experimental data set with k positions of the dipole
t be the template data set
S (x,y) be the predicted position of the dipole
$\epsilon$ be the error between the predicted and actual dipole positions $$r_{k,x,y} = \frac{d_k \cdot t_{x,y}^T}{\sqrt{d_k \cdot d_k^T \cdot t_{x,y} \cdot t_{x,y}^T}}$$

$S(x,y) = \max_{x,y}(r_{k,x,y})$
$\epsilon = S(x,y) - S(x,y)\infty r$

The template can be either from the training data or from modeling. Further, the example algorithm can be used in an analytical approach, an empirical approach, or a hybrid mix.

The modeling approach is provided to improve performance and flexibility of the example training algorithms. Equations for theoretical models will be appreciated by those of ordinary skill in the art. However, some analytical models may not be wholly applicable due to the type of sensor used. Thus, an example empirically developed model is provided according to a nonlimiting embodiment of the present invention.

For the MEMS HWA used in the experiment, and the visual form of the data, it was speculated that a Gaussian mixture model might work well as an empirical model. Gaussian mixtures of the form of Equation 3 were tried.

$$f(x) = \sum_{n=1}^k a_n e^{\left(\left(\frac{-(x-b_n)}{\sqrt{2}\, c_n}\right)^2\right)} \quad (3)$$

From Equation 3, the variable k is referred to as the order of the fit. The first order fit suitably approximates the sensor data, while higher order fits fine-tune the approximation and increase the goodness of fit. FIG. 13 shows the approximation of data collected by a single MEMS HWA sensor by Gaussian fits of the first and second order. The first order fit yielded an $R^2$ value of 0.985 while the second (and successive highorder) fit yielded a 0.997 $R^2$ value. Polynomial fits were also attempted, but were not used due to the complexity of the high-order curves needed for a good fit. Often, as shown in FIG. 13, a ninth-order or higher polynomial curve was needed to achieve a fit with an $R^2$ value of 0.95, less than even a first-order Gaussian curve.

Once an applicable curve was chosen (e.g., two-mixture Gaussian), the curve was fit to all 16 columns of sensor training data. Then, the fitted model was used as a template for the MMSE algorithm. The example algorithm was designed to predict the position of the dipole to within a millimeter using the Gaussian fit. However, to achieve a greater accuracy (e.g., nearest tenth of a millimeter), simple linear interpolation was used between the points of the fit curve. As with training with the raw sensor data, the example MMSE algorithm was used, and three experimental runs were conducted as a test of this approach.

The third example approach, heuristics, includes a set of simple feature-identification methods, similar to those associated in quantitative data processing, imaging, and robotics. Many heuristic methods do not have sufficient formal grounding in statistical signal processing. In part due to this, such methods are often overlooked because of their simplicity and informality.

Figure 14:
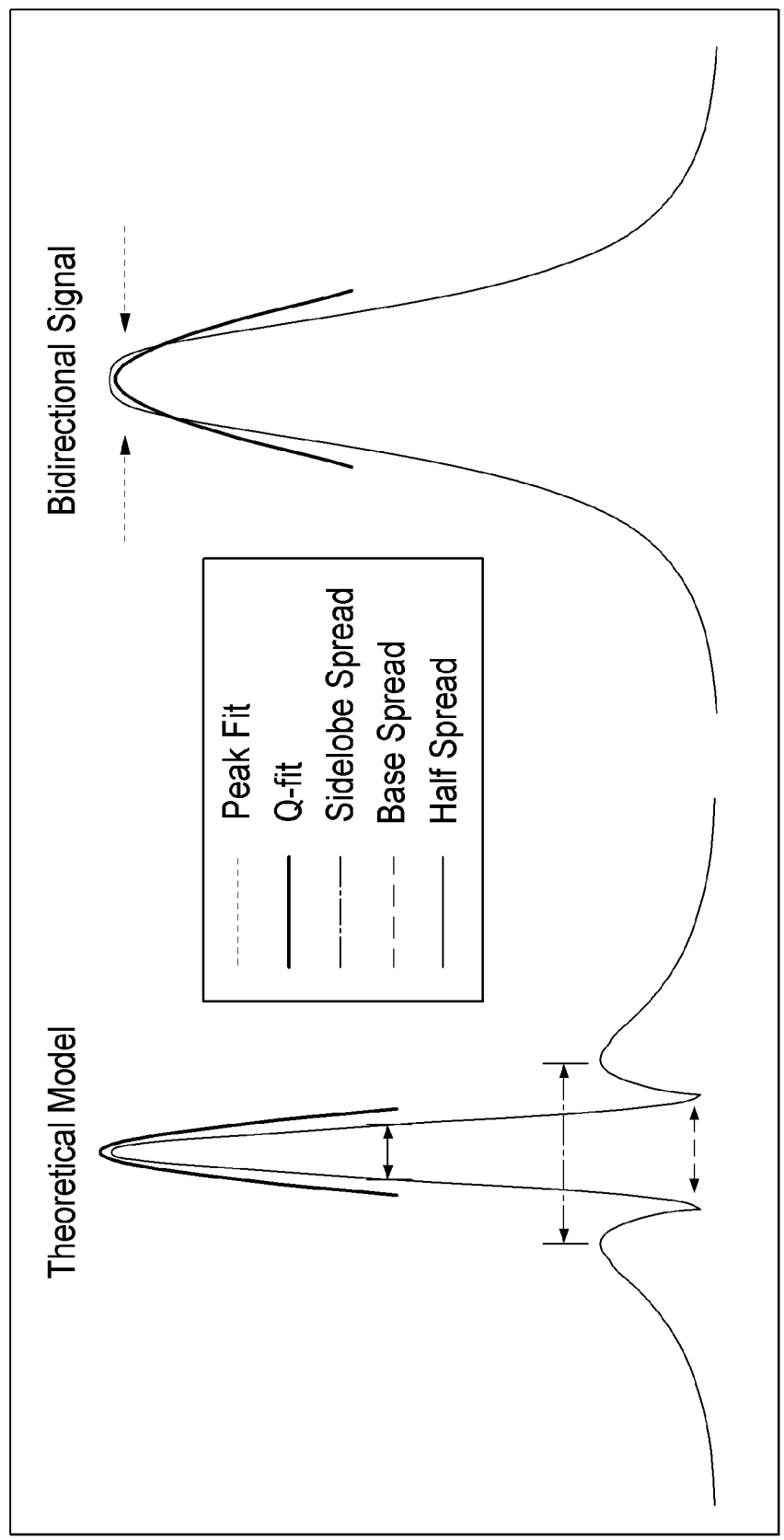
FIG. 14 shows example heuristics for unidirectional (left) and bidirectional (right) models.

Several different types of heuristics are possible, non-limiting examples of which are shown in FIG. 14. Each of the heuristics is described in terms of the features that heuristic mapped to. A peak fit heuristic locates the peak and uses this as a measure of the dipole's actual localization. A Q-fit maps a quadratic fit onto a positive half cycle of a curve. A sidelobe/zero-crossing heuristic uses the sidelobes/zero-crossings as a localization metric. A base spread heuristic uses the base-spanning distance, whereas the half spread heuristic uses the half spread as a metric.

An example localization process with a heuristic approach typically involves training or calibration. An example is given below for the half spread heuristic, though it will be appreciated that other heuristics operate similarly.

I. Conduct horizontal and vertical sweeps at various distances, noting the half spread at each distance. Alternately, this could be done theoretically with an analytical expression, such as an analytical expression for a dipole model. In an example described herein, the response is oriented to a particular sensor, and thus the analytical expression is not used.

II. Using the information in step I, a linear interpolation is used to gather information for intermediate distances. This interpolation is justified, since a linear rate of change can suitably approximate a small dipole traversal.

III. The half spread distance from an experimental run is then matched to the information matrix at hand. This can effectively yield the horizontal and vertical positions given a high Signal-to-Noise Ratio (SNR) environment.

An advantage of this approach lies in its simplicity and ease of implementation. Furthermore, predictive results using the approach, in high SNR cases, are accurate. The disadvantage to this approach is that the performance of the algorithm degrades rapidly as the quality of the environment decreases to the point that, in a low SNR, the results are essentially random.

Figures 15A, 15B:
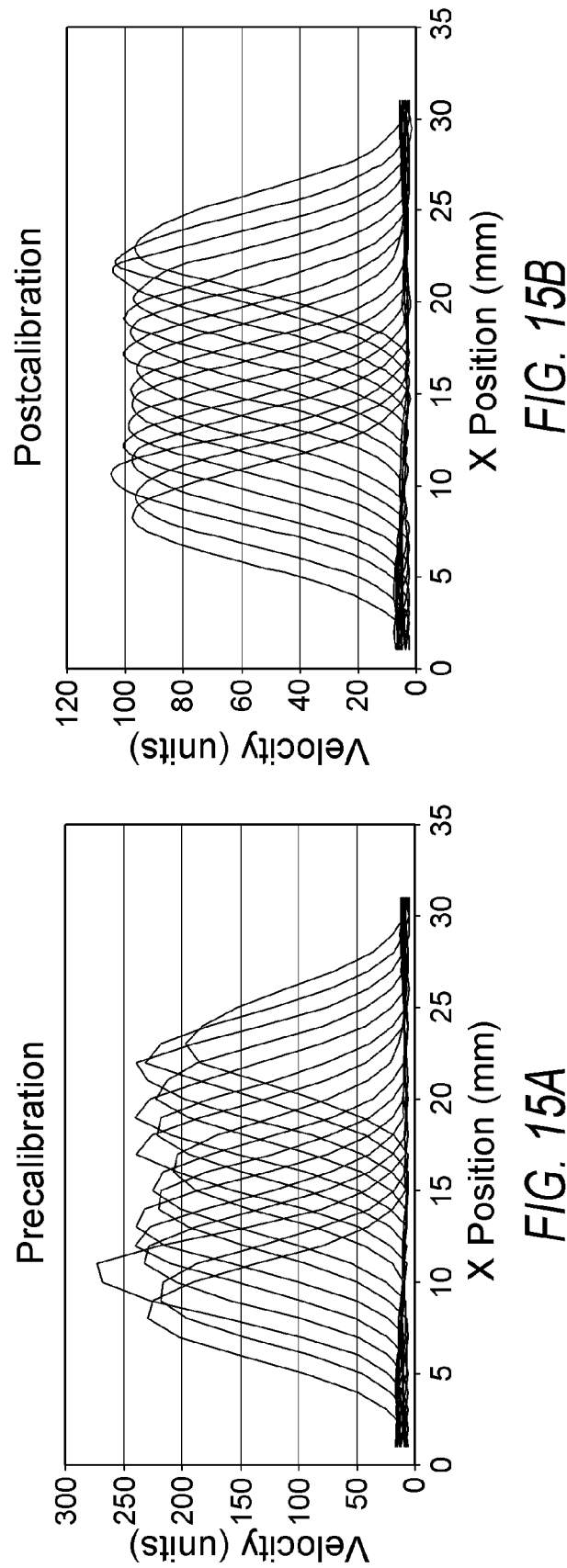
FIG. 15 shows sensor outputs from a training matrix before and after calibration.

Experiments were performed by the present inventors to validate the example algorithms described above. The first step was to calibrate the sensors, to ensure that all sensors exhibit equal sensitivity and to fine-tune the sensors to a common level in software. Due to a preferably fixed spacing of 1 mm between the micromachined sensors, each sensor was shifted by 1 mm, thereby aligning the waveforms for each training matrix. After the alignment, an average was taken of the readings of each position. Each sensor is then calibrated by applying correlation techniques between the averaged and shifted matrices and then normalizing the result to the average. This is done for each of the training matrices. The calibrated data is then rendered in the same form as the training data (coalesced into a three-dimensional set). FIG. 15 shows a series of sensors before and after calibration.

Figure 16:
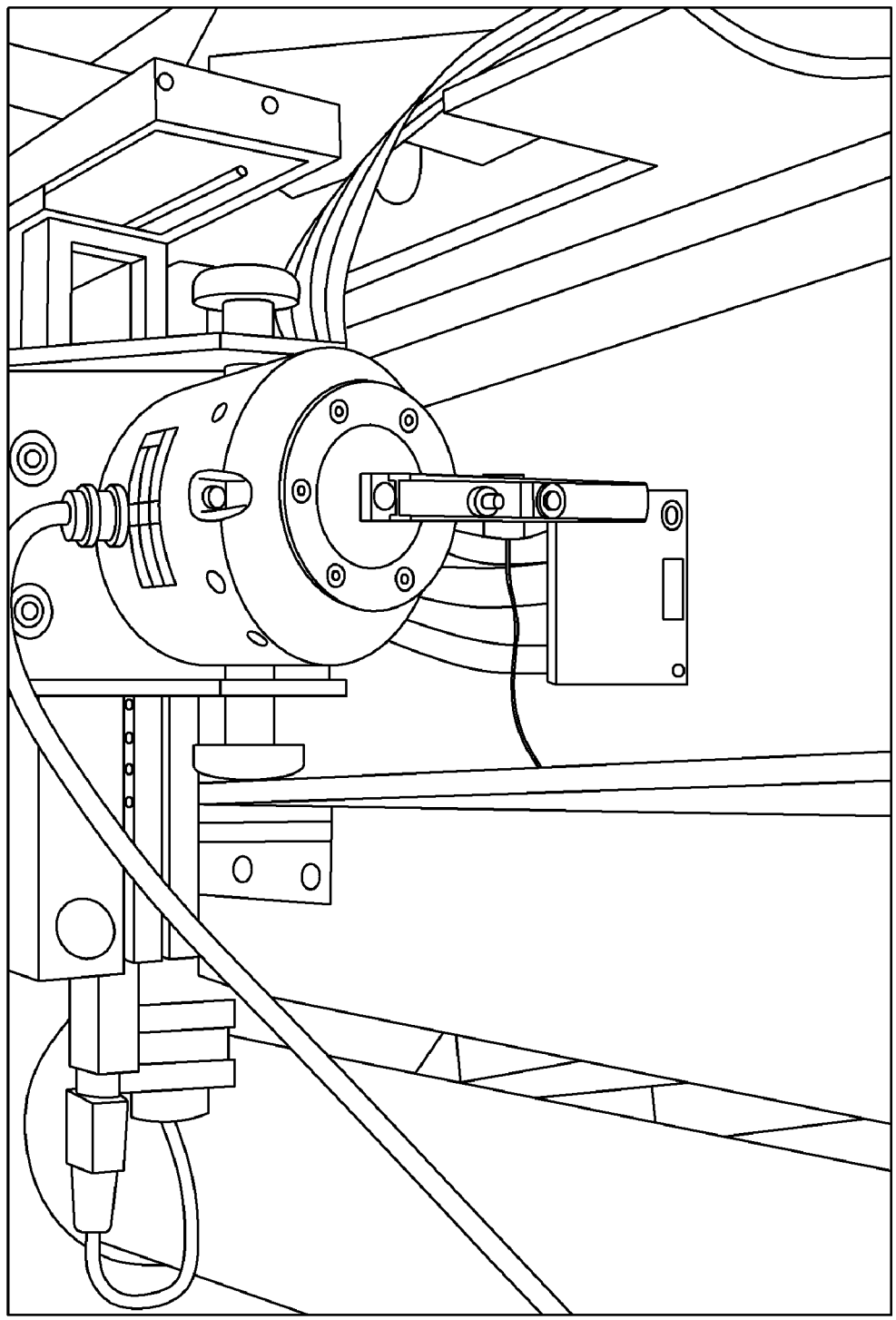
FIG. 16 shows an experimental setup for locating a dipole source.
Figure 17:
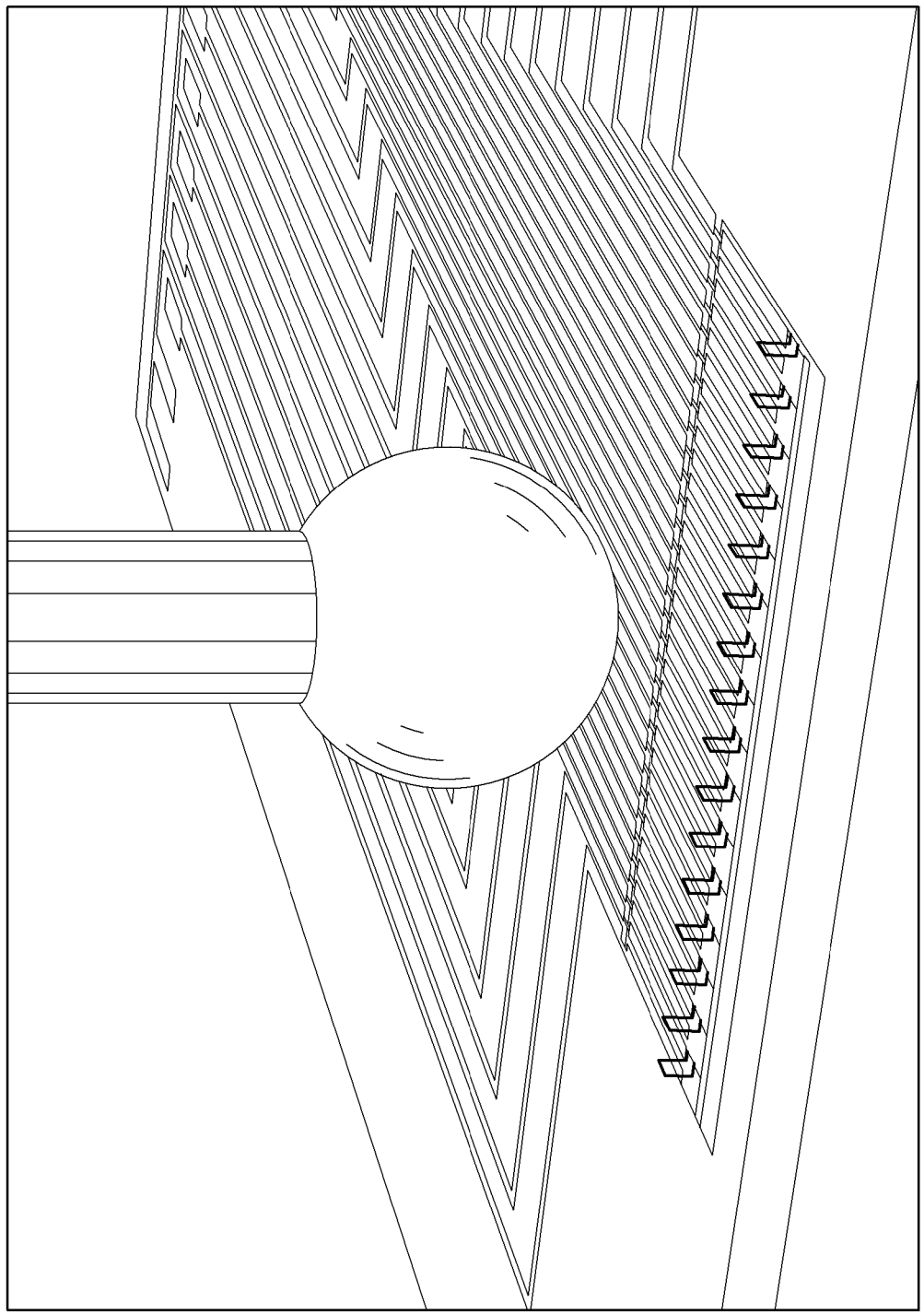
FIG. 17 shows a dipole source.

Hydrodynamic experiments were conducted in a custom-designed water tank. FIG. 16 shows the detailed experimental setup overview, and FIG. 17 shows local details of a dipole source. The setup included a stage system (made by Standa Ltd) for translation control, a minishaker for vibration generation, a sphere to function as a dipole source, and a microfabricated HWA sensor array for sensing and detection. Three linear stages were used, each perpendicularly mounted to the other. Each of them was operated by a stepper motor, which were, in turn, controlled by a computer through a Labview interface. A joint function of three stages can realize an arbitrary three-dimensional movement with accuracy of 2 μm in position. A B&K minishaker (model 4010) was mounted to the stage system. This minishaker can generate sinusoidal vibration along its axis within a frequency range from 2 Hz to 11000 Hz. A 6 mm diasphere is connected to the minishaker through a rod. A PCB accelerometer (model 352B10) was attached to the rod to measure acceleration of vibration.

For these experiments, water was employed as the working fluid. The sphere vibrated in a direction parallel to the axis of the example sensor array, at a fixed frequency of 75 Hz and displacement amplitude of 0.4 mm. For the training approach, systematic measurements were made with the dipole source traveling step-by-step in an area spanning two body-lengths of the sensor array along its axis and one body-length away from it. Experiments were conducted for the dipole source located at each grid point (vertex), with individual grid points 1 mm apart, and with all grid points evenly distributed over the above area. Four runs were taken at each fixed position, i.e., at each specified grid point. For each run, time traces of signal outputs from 16 channels (sensors) were recorded through a computer controlled data acquisition system with a sample rate of 2048 samples/sec and a total length of 1024 samples for each channel. Later, blind runs were recorded as sweeps in the horizontal and vertical directions, or as a composite of sensor values at various positions in the grid. Individual sensor calibration was conducted to accommodate slight differences in sensitivity of each sensor.

Figure 18:
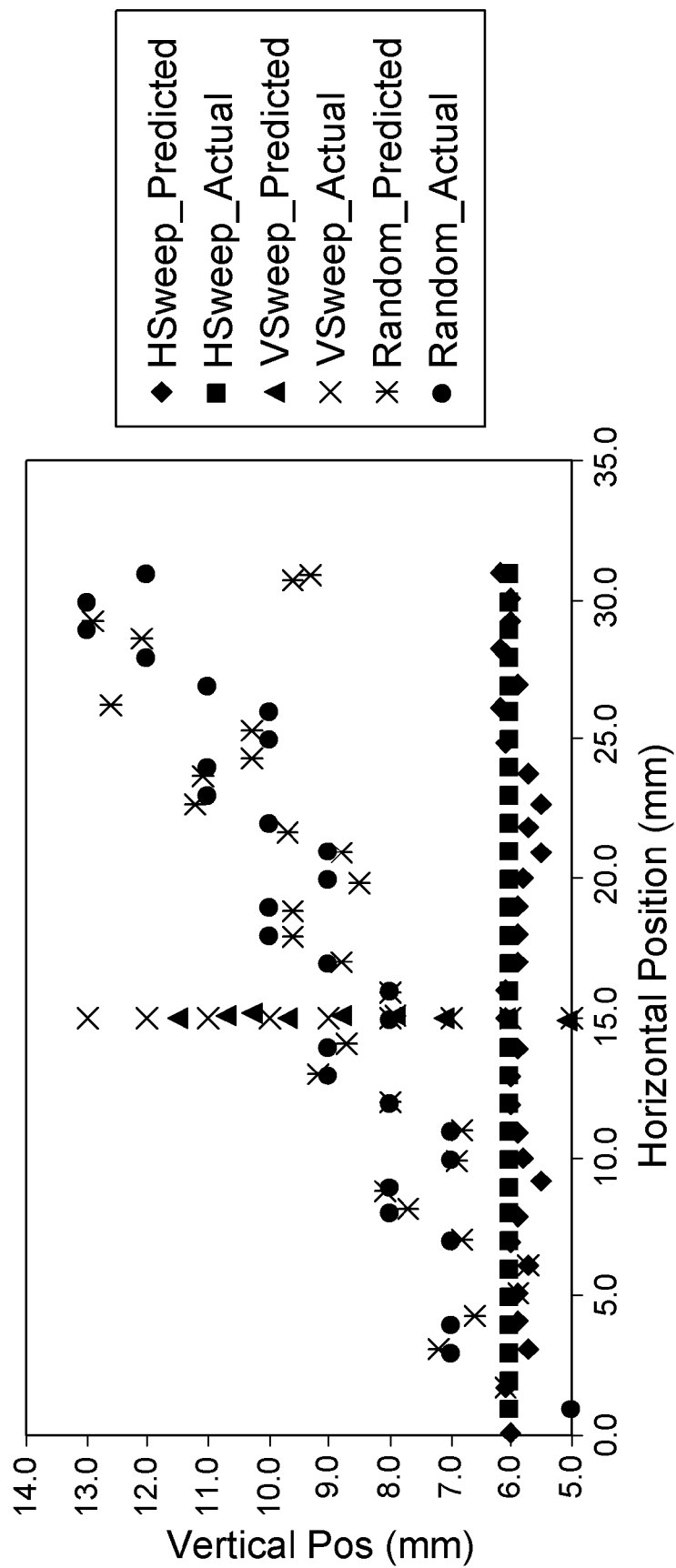
FIG. 18 shows prediction of experimental runs using an example MMSE algorithm and a template training approach.

We used the template training approach to track the location of the dipole source as it moves through the three representative pathways described above. As shown in FIG. 18, the MMSE algorithm accurately predicts the dipole's location along the array (in the x-axis) as well as away from the array (y-axis) in all three cases. The values at the fringes were inaccurate, but performance degradation was expected as the signal decayed and the relative noise increased. Statistically, the accuracy for predicting the location of the dipole decreases as the distance between the dipole and the lateral line increases. The advantage of MMSE is that it lends itself to a fast-real-time implementation and emulation of biological systems. The tradeoff, however, is the processing power and space needed as the predictive space increases.

Figure 19:
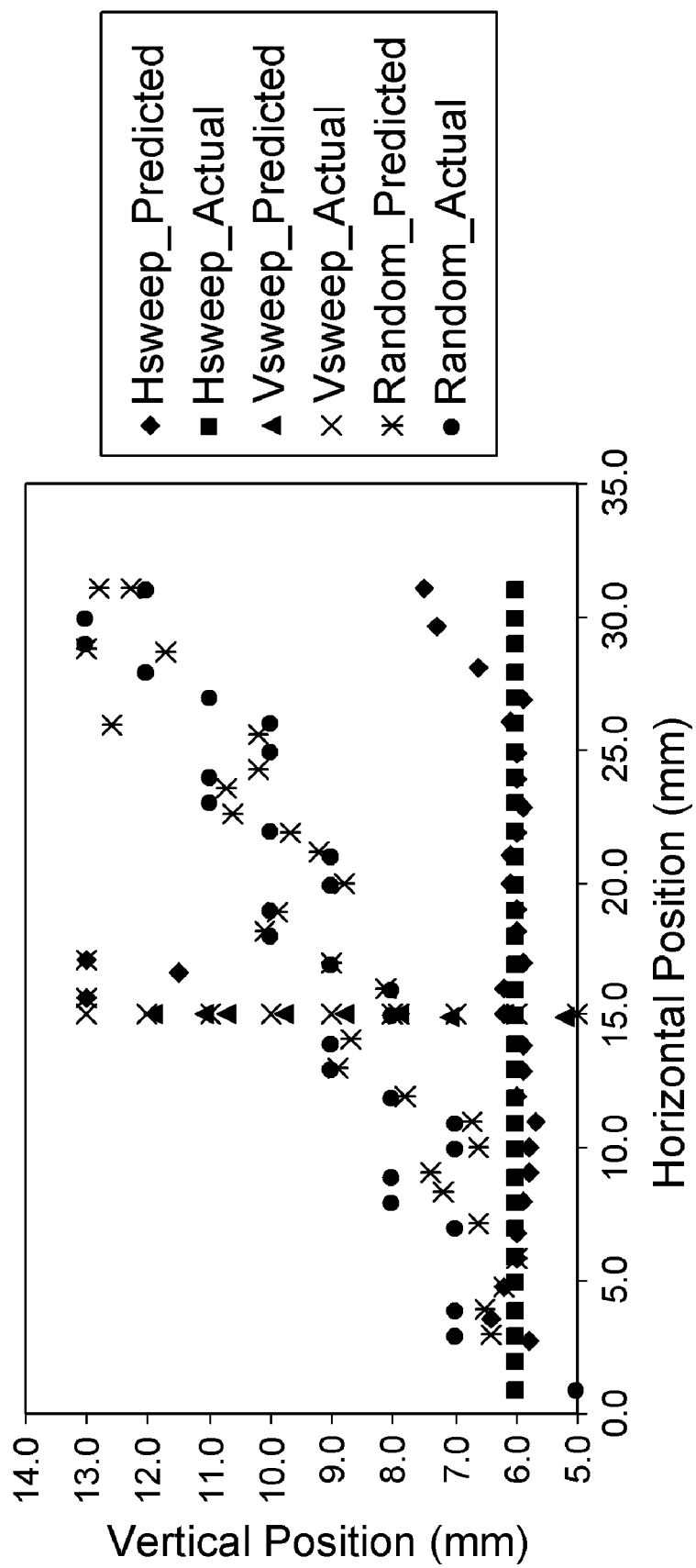
FIG. 19 shows a prediction of experimental runs using an example MMSE algorithm and Gaussian-modeled data.

The modeling approach was used as well to predict the location of the dipole source and tracking its movement, and offered similar results to the MMSE algorithm with raw data. Results obtained using this approach are shown in FIG. 19. Prediction for the vertical run was more accurate, but distortion of the profile as a whole was more pronounced.

The performance of four heuristics, half peak, quadratic fit, sidelobe, and base, is shown in FIG. 20. The line in FIG. 20 shows the actual location of the dipole. As is shown, the accuracy of the heuristic is directly correlated to the SNR level.

In general, example algorithms according to embodiments of the present invention allow localization of a dipole source using an array of microscale MEMS sensors and bio-inspired approaches. Three example approaches include training, modeling, and heuristics.

The training approach provided accurate results using the MMSE algorithm. Furthermore, the example approach can be implemented in a straightforward manner on both static and real-time systems. However, the computational power and raw data set should be significantly large when this approach is applied to complex scenarios. The introduction of variables such as dipole orientation, vibrational frequency and size or a complicated environment involving multiple dipoles would necessitate the use of a much more complex raw data set. Furthermore, while this example approach excels in improving sensor-level robustness, it is vulnerable to system-level changes. For example, reducing the number of sensors or leaving "gaps" (to simulate the failure of individual sensors) was shown to produce near-optimal results. However, significant changes in the orientation or the diameter of the dipole require additional data sets to provide more accurate results.

The heuristic approach likewise is relatively easy to implement in both real-time and static systems. Furthermore, the heuristic approach can handle some degree of error in the environment or on a system-level. Another advantage is that the heuristic approach potentially has the largest range, since it looks for comparisons and is not bound by the size of a fixed data-set grid. However, performance of example heuristic approaches is affected by noise as well as vulnerability to clustered sensor-level failures.

In contrast, the modeling approach is more flexible, and robust. Furthermore, this approach has the accuracy of the training approach while preserving some of the extended range of the heuristic approach. Example methods use a very accurate Gaussian model for MEMS HWA sensors or analytical model for an ideal dipole. At this accuracy, the model closely resembles the underlying data set. Therefore, the model achieves comparable accuracy. However, using such models introduces difficulty and cost in a system-level implementation. This is due to the fact that the raw data sets are pre-fitted to a particular model for the particular array (which, for example, requires additional storage) as well as the fact that scaling should be done before the approach is initially used.

In other example systems, such as, but not limited to, UUV guidance or intrusion detection, a hybrid mix of two or even three approaches would possibly be warranted depending on the application goal and engineering constraints. Different applications such as monitoring and targeting for submarines and ships, port and harbor defense, intrusion detection, and hydro-robotics, as well as different environmental conditions would call for a fusion of both approaches.

Given the example artificial lateral line and example algorithms, we illustrate the capability of this dipole tracking ability using three representative cases. In all tests described below, the dipole was confined to move within an area that covers two body lengths along the artificial lateral line, and one body length away from it, where body length represents the length of the sensor array.

Figure 21A:
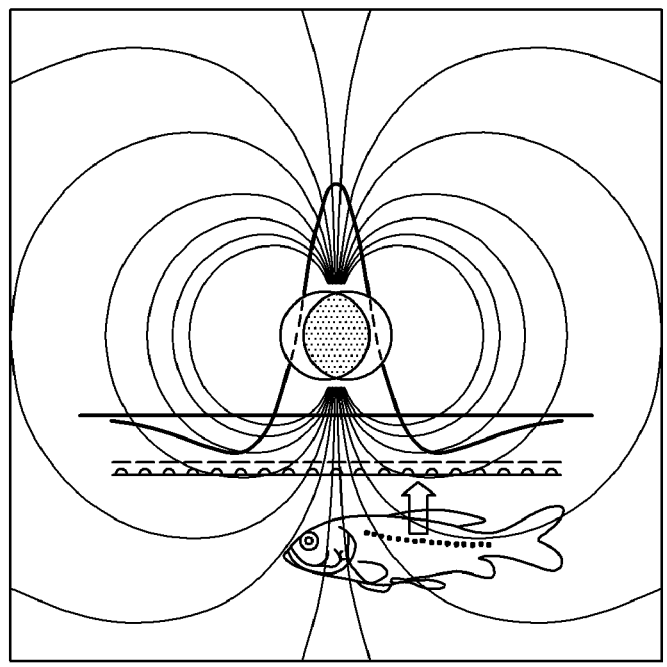
FIG. 21A shows an analytical model of pressure contours (blue lines) and pressure gradient distribution (red line) along a linear array of lateral line canal neuromasts (orange)

A vibrating sphere was employed to function as a dipole source. A minishaker (B&K, model 4010) was fixed to a motorized 3-axis linear stage system (Standa, model 8MT175) equipped with computerized motion control through step motors. A sphere of 3 mm in diameter was attached to the minishaker through a 12-gauge needle that served as the dipole source. An example vibrating sphere is shown in FIG. 21A. An accelerometer (PCB, model 352B10) was attached to the base of the needle to measure the acceleration of the dipole. The artificial lateral line (the packaged HWA array) was mounted on a test fixture rigidly attached to the base of the water tank through a suction cup. For all experiments, arrayed HWA sensors were aligned parallel to the vibration axis of the sphere (i.e., the dipole source), which was operated in sinusoidal mode by the minishaker at a frequency of 75 Hz with displacement amplitude of 0.4 mm.

Theoretical prediction of pressure and pressure gradient felt by a lateral line in response has been made in the past and verified by neuro-physiological studies. The spatial distribution of pressure gradient amplitude resembles a "Mexican hat" profile—the magnitude is highest at the projected center of the dipole and diminishes gradually with increasing lateral distance from the center.

Figure 21B:
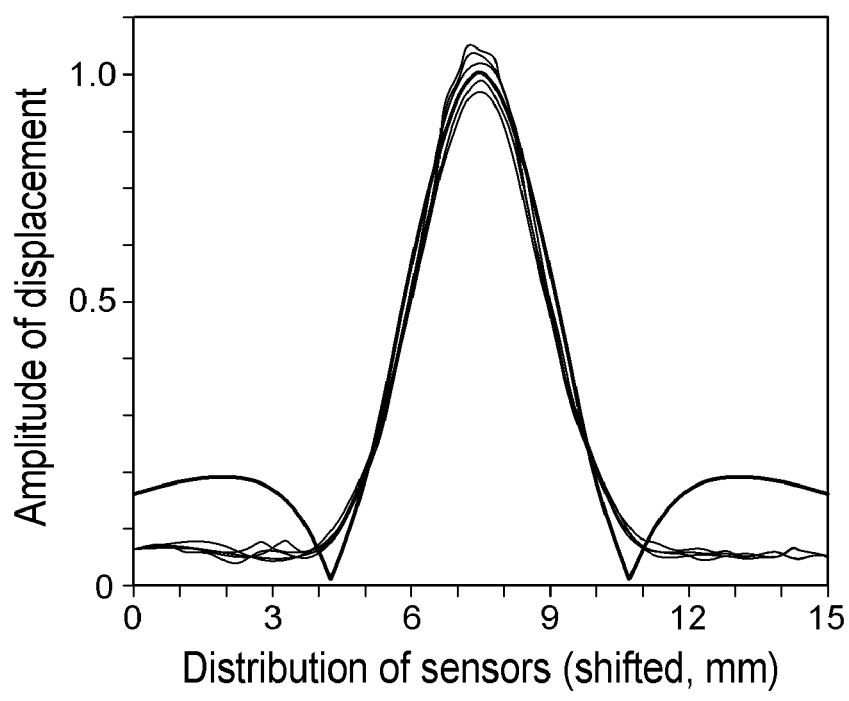
FIG. 21B shows a comparison of experimental (green) and analytical (red) results on displacement amplitude of water particles.

The example artificial lateral line was able to record a profile well matched to the theoretical prediction, as shown in FIG. 21B. This is possible despite the differences between transfer functions of the biological neuromast and the example HWA. It should be noted that the example HWA sensors are subjected to periodic flow sense water particle displacement instead of pressure displacement. However, the values of these two differ only by a factor. The example HWA sensor poses another challenge: namely, it cannot discern the flow polarity and provides a rectified reading of a complex oscillatory flow field. To reconstruct the peak-to-peak amplitude, a derectification technique is used in example methods based on spectrum analysis.

Figure 21D:
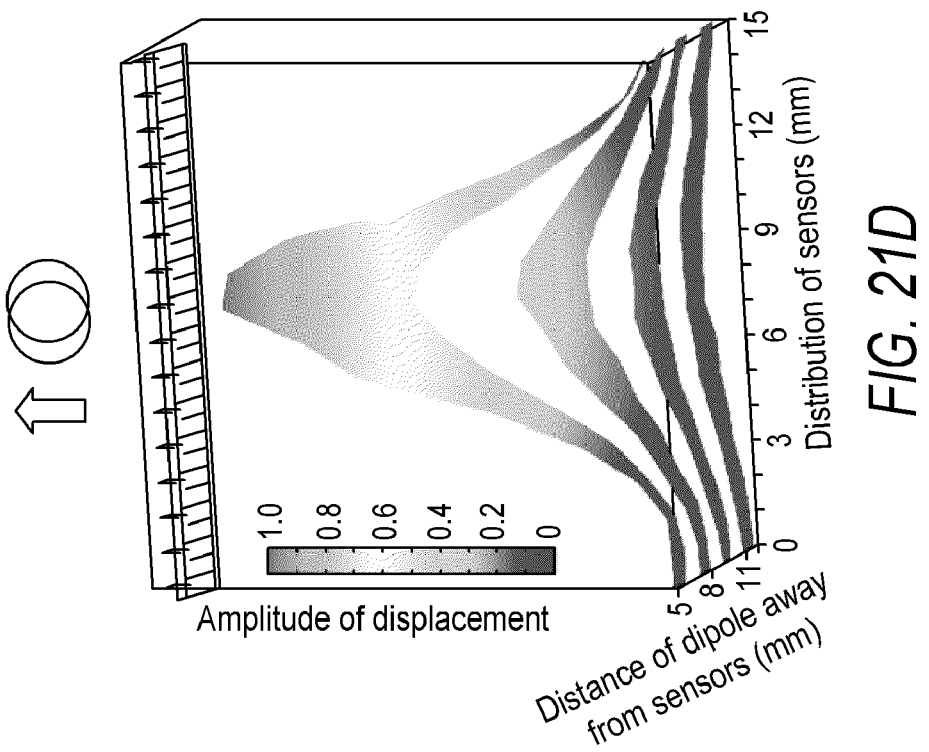
FIG. 21D shows displacement profiles under step-by-step translation following path 2 (as shown in FIG. 21E)
Figure 21C:
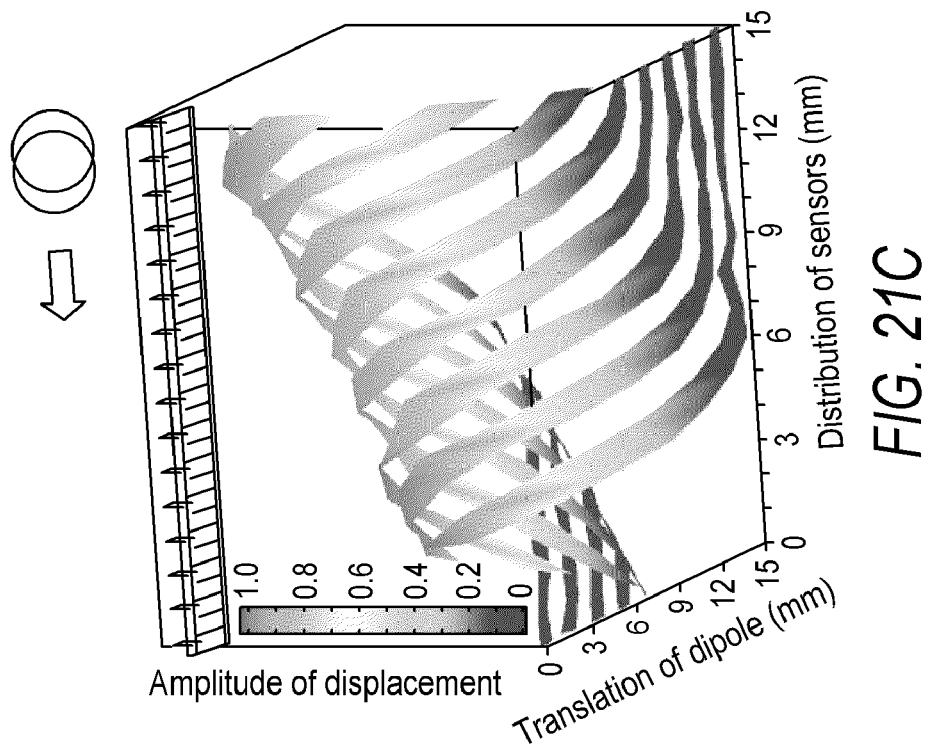
FIG. 21C shows time-elapsed spatial profiles of displacement amplitude with step-by-step translation of the dipole source along an example artificial lateral line following path 1 (as shown in FIG. 21E)
Figure 21E:
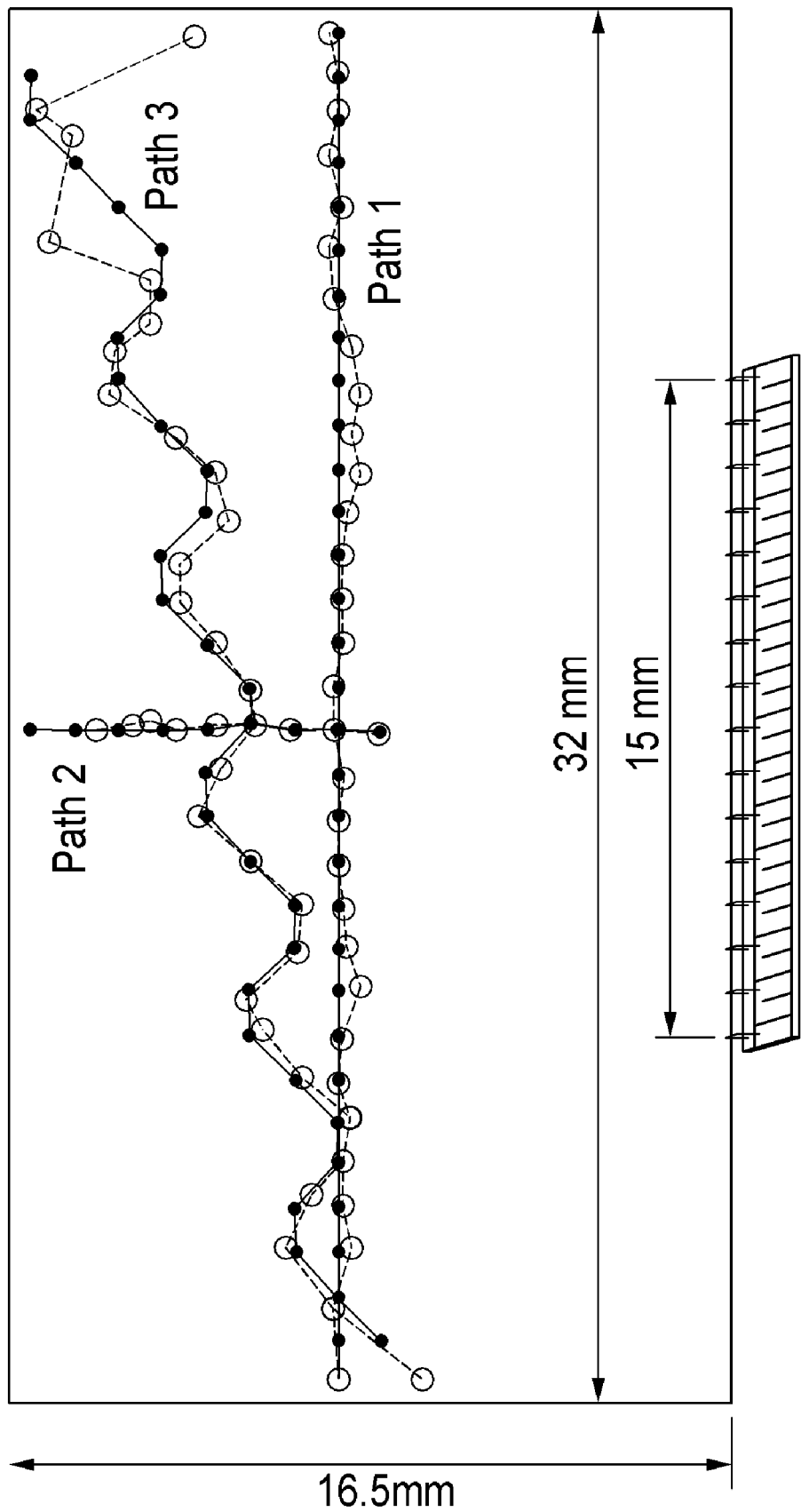
FIG. 21E shows a comparison of actual (solid) and predicted (dashed) paths.

In the first representative case, the dipole source is translated stepwise parallel to the artificial lateral line path, as shown in path 1 of FIG. 21E. The lateral output recorded at each step has identical amplitude with shifting apex, as shown in FIG. 21C. In the second representative case, the dipole source is moved perpendicularly away from the lateral line. The profiles of lateral line output flatten out when the dipole source fades into the distance, as shown in FIG. 21D. In a third case, the dipole traverses in a complex path in the plane of the sensor array. For the three paths, predictions are very accurate in most locations, and generally become less accurate with increased distance from the sensor array.

In addition to localization of a swimming prey in a dipolar near field, following the wake behind the prey can allow a predator to track and eventually localize the prey, starting at a much greater distance (e.g., a few to a few tens of prey-body length). It has been shown that a functional lateral line can be used for wake following.

Figure 22:
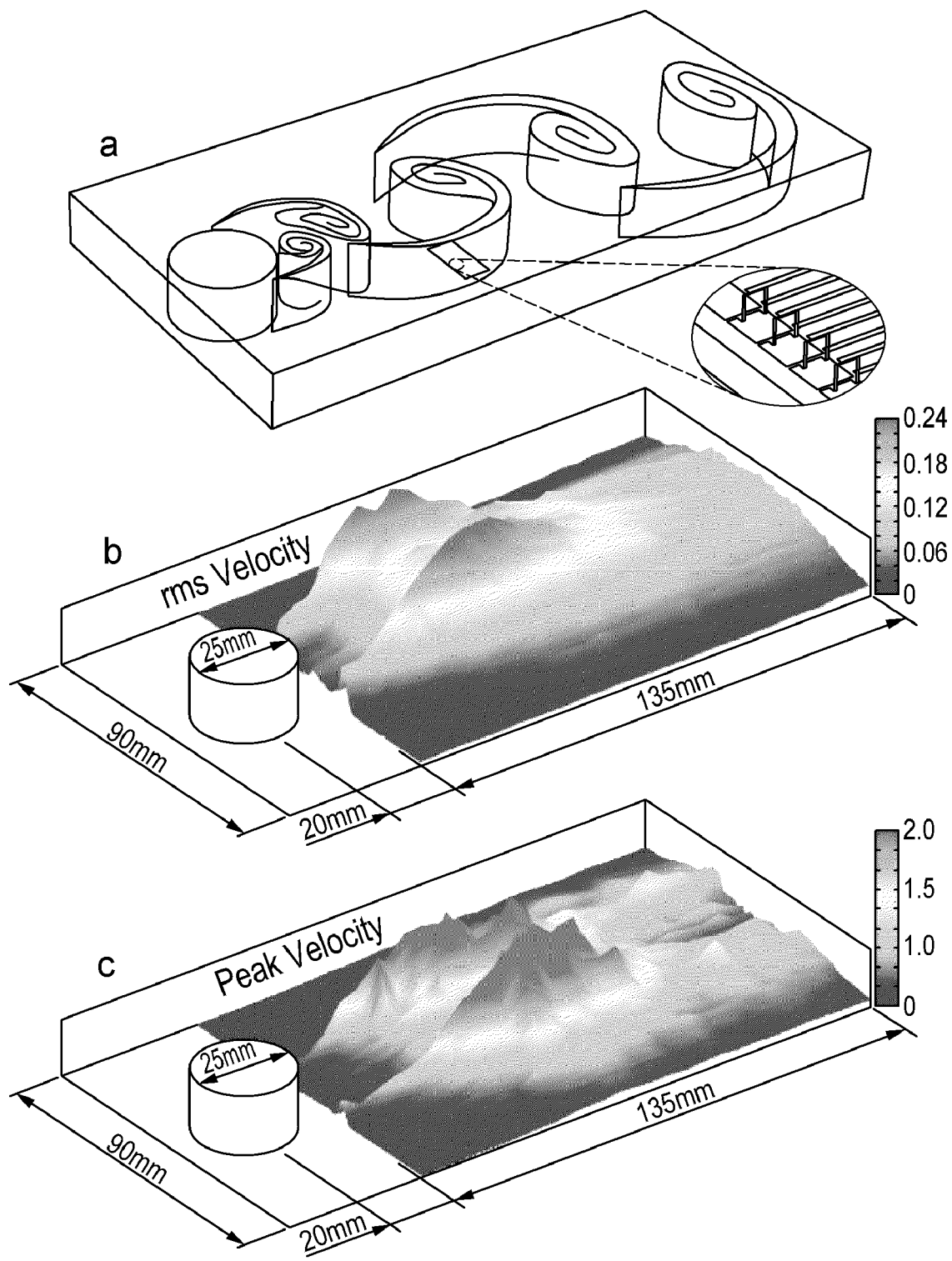
FIG. 22A shows an experimental setup for wake tracking.
FIG. 22B shows patterns of rms water velocity at vortex shedding frequency in the wake of a cylinder, normalized by free-stream inflow velocity.
FIG. 22C shows patterns of peak water velocity at vortex shedding frequency in the wake of a cylinder, normalized by free-stream inflow velocity.

The wake behind a swimming fish contains organized vortices. Inspired by this, we generated a turbulent wake by using a vertically mounted circular cylinder placed in water flow (Re=5000), as shown in FIGS. 22A-22C. The wake includes alternately shed large-scale vortices known as a Kármán Street, as shown in FIG. 22A. The strength of the vortices is similar to those produced by certain freely swimming fish. We find that by using the example artificial lateral line, one can identify the signature of a wake and the general direction of the source.

A desktop water tunnel (ELD Inc., model 501) with a test section of 150 mm by 150 mm was employed. A cylinder of 25 mm in diameter was vertically fixed in a uniform current at speed of 0.2 m/s. The corresponding Reynolds number is approximately 5000. The example artificial lateral line was exposed in the wake behind the cylinder with arrayed HWA sensors perpendicular to the inflow and to the axis of the cylinder. The PC board holding the substrate where sensors resided was tilted at an angle of attack of 5° to suppress flow separation from the leading edge on the sensor side. To correct sensitivity difference among sensors, and to correct the non-linear response of each individual sensor, the sensor array was calibrated under the same condition without the cylinder.

The example artificial lateral line was exposed to the wake to record the spatial distribution of local velocity fluctuation. To cover the desired size of the field of view (3.5D wide and 6D deep, with D being the diameter of the cylinder), we traversed the sensor array across the wake and stitched multiple images, as shown in FIG. 22A.

The distribution of rms velocity (FIG. 22B) shows that the example lateral line array is capable of capturing the main feature of the wake: dramatic dual peaks with a valley in between in the near wake, and decreasing intensity of the peaks further downstream.

The velocity fluctuation (FIG. 22C) was determined using a second method that accentuates peak features with even greater contrast. This method includes extracting the flow velocity amplitude at a characteristic frequency associated with the wake-generating source, e.g., the vortex shedding frequency from the cylinder. As a result, two clearly defined peaks occurred along the entire field of view. We conjecture that this algorithm lowers the background signal by rejecting broadband noise in the fluid.

Example artificial lateral lines have been shown to have significant flow sensing capability. The high velocity sensitivity (200 μm/s) and broad bandwidth (1 KHz) enable the artificial lateral line to sense minute variation of diverse hydrodynamic events. The dense arrangement of individual microscale sensors (e.g., spacing of 1 mm) provides high spatial resolution on both global patterns and local details. Omni-directional sensing with high resolution is possible in certain embodiments. Assisted with example algorithms, collected information from a sensor array of the example artificial lateral line can be used for localization, and tracking, of underwater moving objects. Such functionalities endow the example artificial lateral line with the unique sense of distant touch. Equipped with this technique, underwater vehicles or objects can gain a new sense in addition to vision and sonar. That, in turn, can significantly enhance the capability of underwater vehicles and objects of target detection and following, as well as collision avoidances, especially under circumstances when vision and sonar abilities are limited.

Artificial lateral lines according to exemplary embodiments of the present invention may be useful for, as nonlimiting examples: comprehensive monitoring of a liquid flow field for underwater vehicles and structures, such as autonomous underwater vehicles, deep-sea drilling stations, and military vehicles; comprehensive monitoring of flow conditions for aircrafts and unmanned vehicles; or more generally as a large sensitive skin for covering an object, for providing characterization of a flow field, object source localization, wave tracking, chemical sensing, etc.

Example applications of the artificial lateral line can provide a new mode of hydrodynamic sensing, including distant touch sensing similar to a lateral line of fish. Stealth identification of underwater objects is possible, with high spatial resolution, and even stealth imaging without revealing one's presence and/or position, unlike some imaging based on vision or sonar. Example artificial lateral lines can provide information for control methods for underwater vehicles.

While various embodiments of the present invention have been shown and described, it should be understood that other modifications, substitutions, and alternatives are apparent to one of ordinary skill in the art. Such modifications, substitutions, and alternatives can be made without departing from the spirit and scope of the invention, which should be determined from the appended claims.

Various features of the invention are set forth in the appended claims.

What is claimed is:

1. An artificial sensor, comprising:
   at least one substrate;
   a plurality of flow sensors disposed on said at least one substrate for providing a plurality of spatial-temporally varying signals representing a hydrodynamic stimulus, said plurality of flow sensors being spatially distributed on said at least one substrate; and
   a processor coupled to said plurality of flow sensors for receiving the signals and determining spatial-temporal information from the received signals.

2. The artificial sensor of claim 1, wherein said plurality of flow sensors include at least one hot-wire anemometer sensor.

3. The artificial sensor of claim 2, wherein each of the at least one hot-wire anemometer sensor comprises:
   a flow sensing element;
   at least one cantilever disposed on the substrate and supporting said flow sensing element in a raised position with respect to said substrate.

4. The artificial sensor of claim 3, wherein said flow sensing element comprises a nickel wire.

5. The artificial sensor of claim 1, wherein said plurality of flow sensors are disposed in a linear array.

6. The artificial sensor of claim 1, wherein said plurality of flow sensors are disposed in a two-dimensional array.

7. The artificial sensor of claim 1, wherein said plurality of flow sensors are disposed in an array having a substantially constant spacing.

8. The artificial sensor of claim 1, further comprising:
   a covering for said substrate, said covering including a canal disposed over said substrate and a plurality of pores extending from a surface of said covering to the canal;
   wherein said plurality of flow sensors are disposed along the canal.

9. A method for flow sensing, comprising:
   receiving spatial and temporal flow input signals from a plurality of flow sensors spatially disposed along a substrate;
   comparing said received input signals to a predetermined flow source location;
   based on said comparing, predicting a flow source location.

10. The method of claim 9, wherein said predicting comprises:
    if an error between said received input signals and the predetermined flow source location is minimal, determining that the predetermined flow source location is the predicted flow source location.

11. The method of claim 9, wherein the predetermined flow source location is determined based on previously-received sensor input data.

12. The method of claim 9, wherein the predetermined flow source location is determined based on a model.

13. The method of claim 9, wherein the predetermined flow source location is determined based on previously-received sensor input data and a model.

14. The method of claim 9, wherein the predetermined flow source location is determined based on a matrix created using previously-received sensor input data.

15. The method of claim 9, wherein the predetermined flow source location is determined based on a model, and wherein the model is formed using linear interpolation.

16. A method for flow sensing, comprising:
receiving spatial and temporal flow input signals from a plurality of flow sensors spatially disposed along a substrate;
comparing said received input signals to a metric based on a heuristic;
determining a flow source location based on said comparing.

* * * * *